(12) United States Patent
Schneider et al.

(10) Patent No.: US 6,537,432 B1
(45) Date of Patent: Mar. 25, 2003

(54) PROTEIN SEPARATION VIA MULTIDIMENSIONAL ELECTROPHORESIS

(75) Inventors: Luke V. Schneider, Half Moon Bay, CA (US); Michael P. Hall, San Carlos, CA (US); Robert Petesch, Newark, CA (US)

(73) Assignee: Target Discovery, Inc., Palo Alto, CA (US)

( * ) Notice: Subject to any disclaimer, the term of this patent is extended or adjusted under 35 U.S.C. 154(b) by 0 days.

(21) Appl. No.: 09/513,486

(22) Filed: Feb. 25, 2000

Related U.S. Application Data

(60) Provisional application No. 60/130,238, filed on Apr. 20, 1999, and provisional application No. 60/075,715, filed on Feb. 24, 1998.

(51) Int. Cl.[7] .............................................. B01D 57/02
(52) U.S. Cl. ........................ 204/450; 204/451; 204/601
(58) Field of Search ................................ 204/602, 451, 204/455, 601, 605, 450

(56) References Cited

U.S. PATENT DOCUMENTS

| 4,690,749 A | 9/1987 | Van Alstine et al. |
| 4,725,343 A | 2/1988 | Hjerten et al. |
| 4,842,701 A | 6/1989 | Smith et al. ............. 204/180.1 |
| 4,859,301 A | 8/1989 | Brenner et al. |
| 4,911,808 A | 3/1990 | Hjerten |
| 4,931,328 A | 6/1990 | Swedberg |
| 4,994,165 A | 2/1991 | Lee et al. ............... 204/299 R |
| 4,997,536 A | 3/1991 | Ohms et al. |
| 5,015,350 A | 5/1991 | Wiktorowicz |
| 5,074,982 A | 12/1991 | Novotny et al. |

(List continued on next page.)

FOREIGN PATENT DOCUMENTS

WO    WO 95/33989    * 12/1995    ................ 27/447

OTHER PUBLICATIONS

Mann and Wilm, "Error–Tolerant Identification of Peptides in Sequence Databases by Peptide Sequence Tags", *Anal. Chem.*, 66:(24) 4390–4399 (Dec. 15, 1994).

Jensen et al., "Sequence patterns produced by incomplete enzymatic digestion or one–step Edman degradation of peptide mixtures as probes for protein database searches", *Electrophoresis*, 17:938–944 (1996).

Wilkins et al., "Protein identification with sequence tags", *Current Biology*, 6(12):1543–1544 (1996).

Wilkins et al., "Rapid Protein Identification Using N–Terminal "Sequence Tag" and Amino Acid Analysis", *Biochemical and Biophysical Research Communications*, 221: 609–613, (1996) Article No. 0643.

Wilkins et al., "Protein Identification with N and C–Terminal Sequence Tags in Proteome Projects", *J. Mol. Biol.*, 278: 599–608 (1998).

Jensen, et al. "Sequence Patterns Produced by Incomplete Ezymatic Digestion or One–step Edman Degradation of Peptide Mixture as Probes for Protein Database Searches" *Electrophoresis* (1996) vol. 15(5); pp. 938–944.

(List continued on next page.)

*Primary Examiner*—Jill Warden
*Assistant Examiner*—Sam P. Siefke
(74) *Attorney, Agent, or Firm*—Townsend and Townsend and Crew LLP

(57) ABSTRACT

The present method provides methods and apparatus for separating proteins using a series of electrophoretic methods that utilize controlled fractionation and labeling techniques to resolve mixtures of proteins. The samples for each electrophoretic method other than the initial method, contain only a subset of proteins resolved in the preceding method. The methods can be used in a variety of different applications including, creating proteomic databases, comparative expression studies, diagnostics, structure activity relationships and metabolic engineering investigations.

55 Claims, 10 Drawing Sheets

U.S. PATENT DOCUMENTS

| | | |
|---|---|---|
| 5,096,554 A | 3/1992 | Chin |
| 5,110,424 A | 5/1992 | Chin |
| 5,110,434 A | 5/1992 | Zhu et al. |
| 5,143,753 A | 9/1992 | Novotny et al. |
| 5,180,475 A | 1/1993 | Young et al. |
| 5,181,999 A | 1/1993 | Wiktorowicz |
| 5,240,585 A | 8/1993 | Young et al. |
| 5,262,031 A | 11/1993 | Lux et al. |
| 5,282,942 A | 2/1994 | Herrick |
| 5,290,587 A | 3/1994 | Young et al. |
| 5,306,412 A | 4/1994 | Whitehouse et al. ... 204/299 R |
| 5,314,593 A | 5/1994 | Swedberg |
| 5,320,730 A | 6/1994 | Ewing et al. |
| 5,322,608 A | 6/1994 | Karger et al. |
| 5,358,618 A | 10/1994 | Ewing et al. |
| 5,378,334 A | 1/1995 | Dadoo et al. |
| 5,391,274 A | 2/1995 | Shieh |
| 5,415,747 A | 5/1995 | Holloway et al. |
| 5,429,728 A | 7/1995 | Gordon |
| 5,441,613 A | 8/1995 | McCormick |
| 5,447,617 A | 9/1995 | Shieh |
| 5,462,646 A | 10/1995 | Shieh |
| 5,505,832 A | 4/1996 | Laukien et al. ............. 204/452 |
| 5,599,432 A * | 2/1997 | Manz et al. ................ 204/451 |
| 5,611,903 A | 3/1997 | Janssens et al. |
| 5,792,331 A | 8/1998 | Srinivasan et al. |
| 5,840,388 A | 11/1998 | Karger et al. |
| 5,856,082 A | 1/1999 | Aebersold et al. ............. 435/4 |
| 5,872,010 A | 2/1999 | Karger et al. ............... 436/173 |
| 6,074,542 A | 6/2000 | Dolnik et al. |
| 6,103,199 A * | 8/2000 | Bjornson .................... 422/100 |
| 6,297,099 B1 | 10/2001 | Hsich et al. |
| 6,372,353 B2 | 4/2002 | Karger et al. |
| 6,375,818 B1 | 4/2002 | Huang et al. |

OTHER PUBLICATIONS

Li, et al. "Improvements on Sample Handling for Rapid Mass Spectrometric Identification of Proteins Resolved by 2D Gel Electrophoresis" *Book of Abstracts, 213th ACS National Meeting, San Francisco* (Apr. 13–17, 1997).

Mann, et al. "Error–Tolerant Identification of Peptides in Sequence Databases by Peptide Sequence Tags" *Analytical Chemistry* (Dec. 15, 1994) vol. 66(24), pp. 4390–4399.

Wilkins, et al. "Protein Identification with Sequence Tags" *Current Biology* (1996) vol. 6(12), pp. 1543–1544.

Wilkins, et al. "Rapid Protein Identification Using N–terminal 'Sequence Tag' and Amino Acid Analysis" *Biochemical and Biophysical Research Communications* (1996) vol. 221(3), pp. 609–613.

Wilkins, et al. "Protein Identification with N and C–terminal Sequence Tags in Proteome Projects" *J. Mol. Biol.* (*1998*) vol. *278*(*3*), pp. *599–608*.

* cited by examiner

PROTEIN SEPARATION VIA MULTIDIMENSIONAL ELECTROPHORESIS

CROSS-REFERENCES TO RELATED APPLICATIONS

This application claims the benefit of U.S. provisional application No. 60/130,238 filed Apr. 20, 1999. This application is also related to U.S. provisional application No. 60/075,715 filed Feb. 24, 1998, U.S. patent application Ser. No. 09/513,395, filed Feb. 25, 2000, now U.S. Pat. No. 6,379,971, and copending U.S. application Ser. No. 09/513,907, filed Feb. 25, 2000. All of these applications are incorporated by reference in their entirety for all purposes.

FIELD OF THE INVENTION

This invention relates to the field of protein separation and proteomics.

BACKGROUND OF THE INVENTION

A goal of genomics research and differential gene expression analysis is to develop correlations between gene expression and particular cellular states (e.g., disease states, particular developmental stages, states resulting from exposure to certain environmental stimuli and states associated with therapeutic treatments). Such correlations have the potential to provide significant insight into the mechanism of disease, cellular development and differentiation, as well as in the identification of new therapeutics, drug targets and/or disease markers. Correlations of patterns of gene expression can also be used to provide similar insights into disease and organism metabolism that can be used to speed the development of agricultural products, transgenic species, and for metabolic engineering of organisms to increase bioproduct yields or desirable metabolic activities.

Many functional genomic studies focus on changes in mRNA levels as being indicative of a cellular response to a particular condition or state. Recent research, however, has demonstrated that often there is a poor correlation between gene expression as measured by mRNA levels and actual active gene product formed (i.e., protein encoded by the mRNA). This finding is not surprising since many factors-including differences in translational efficiency, turnover rates, extracellular expression or compartmentalization, and post-translational modification affect protein levels independently of transcriptional controls. Thus, the evidence indicates that functional genomics is best accomplished by measuring actual protein levels (i.e., utilizing proteomic methods) rather than with nucleic acid based methods. The successful use of proteins for functional genomic analyses, however, requires reproducible quantification of individual proteins expressed in cell or tissue samples.

Two-dimensional (2-D) gel electrophoresis is currently the most widely adopted method for separating individual proteins isolated from cell or tissue samples [5, 6, 7]. Evidence for this is seen in the proliferation (more than 20) of protein gel image databases, such as the Protein-Disease Database maintained by the NIH [8]. These databases provide images of reference 2-D gels to assist in the identification of proteins in gels prepared from various tissues.

Capillary electrophoresis (CE) is a different type of electrophoresis, and involves resolving components in a mixture within a capillary to which an electric field is applied. The capillary used to conduct electrophoresis is filled with an electrolyte and a sample introduced into one end of the capillary using various methods such as hydrodynamic pressure, electroosmotically-induced flow, and electrokinetic transport. The ends of the capillary are then placed in contact with an anode solution and a cathode solution and a voltage applied across the capillary. Positively charged ions are attracted towards the cathode, whereas negatively charged ions are attracted to the anode. Species with the highest mobility travel the fastest through the capillary matrix. However, the order of elution of each species, and even from which end of the capillary a species elutes, depends on its apparent mobility. Apparent mobility is the sum of a species electrophoretic mobility in the electrophoretic matrix and the mobility of the electrophoretic matrix itself relative to the capillary. The electrophoretic matrix may be mobilized by hydrodynamic pressure gradients across the capillary or by electroosmotically-induced flow (electroosmotic flow).

A number of different electrophoretic methods exist. Capillary isoelectric focusing (CIEF) involves separating analytes (such as proteins) within a pH gradient according to the isoelectric point (i.e., the pH at which the analyte has no net charge) of the analytes. A second method, capillary zone electrophoresis (CZE) fractionates analytes on the basis of their intrinsic charge-to-mass ratio. Capillary gel electrophoresis (CGE) is designed to separate proteins according to their molecular weight. (For reviews of electrophoresis generally, and CIEF and CZE specifically, see, e.g., Palmieri, R. and Nolan, J. A., "Protein Capillary Electrophoresis: Theoretical and Experimental Considerations for Methods Development," in *CRC Handbook of Capillary Electrophoresis: A Practical Approach*, CRC Press, chapter 13, pp. 325–368 (1994); Kilar, F., "Isoelectric Focusing in Capillaries," in *CRC Handbook of Capillary Electrophoresis: A Practical Approach*, CRC Press, chapter 4, pp. 95–109 (1994); and McCormick, R. M., "Capillary Zone Electrophoresis of Peptides," in *CRC Handbook of Capillary Electrophoresis: A Practical Approach*, CRC Press, chapter 12, pp. 287–323 (1994). All of these references are incorporated by reference in their entirety for all purposes).

While 2-D gel electrophoresis is widely practiced, several limitations restrict its utility in functional genomics research. First, because 2-D gels are limited to spatial resolution, it is difficult to resolve the large number of proteins that are expressed in the average cell (1000 to 10,000 proteins). High abundance proteins can distort carrier ampholyte gradients in capillary isoelectric focusing electrophoresis and result in crowding in the gel matrix of size sieving electrophoretic methods (e.g., the second dimension of 2-D gel electrophoresis and CGE), thus causing irreproducibility in the spatial pattern of resolved proteins [20, 21 and 22]. High abundance proteins can also precipitate in a gel and cause streaking of fractionated proteins [20]. Variations in the crosslinking density and electric field strength in cast gels can further distort the spatial pattern of resolved proteins [23, 24]. Another problem is the inability to resolve low abundance proteins neighboring high abundance proteins in a gel because of the high staining background and limited dynamic range of gel staining and imaging techniques [25, 22]. Limitations with staining also make it difficult to obtain reproducible and quantifiable protein concentration values, with average standard variations in relative protein abundance between replicate 2-D gels reported to be 20% and as high as 45% [4]. In some recent experiments, for example, investigators were only able to match 62% of the spots formed on 3–7 gels run under similar conditions [21; see also 28, 29]. Additionally, many proteins are not soluble in buffers compatible with acrylamide gels, or fail to enter the gel efficiently because of their high molecular weight [26, 27].

SUMMARY OF THE INVENTION

The present invention provides a variety of electrophoretic methods and apparatus for separating mixtures of proteins. The methods involve conducting multiple capillary electrophoresis methods in series, wherein samples for each method other than the initial method contain only a subset of the proteins from the preceding step (e.g., from fractions containing resolved protein from the preceding method). By using a variety of techniques to control elution during electrophoresis, the methods are capable of resolving proteins in even complex mixtures such as obtained from tissues and native cells. Utilizing various labeling schemes and detection methods, certain methods can provide quantitative information on the amount of each of the separated proteins. Such information can be used in the development of protein databases in which proteins expressed under certain conditions are characterized and catalogued. Comparative studies to identify proteins that are differentially expressed between different types of cells or tissues can also be conducted with the methods of the present invention. The methods can also be used in diagnostic, structure activity and metabolic engineering studies.

In general, the methods involve performing a plurality of electrophoretic methods in series. Each method in the series includes electrophoresing a sample containing multiple proteins to obtain a plurality of resolved proteins. The sample that is electrophoresed contains only a subset of the plurality of resolved proteins from the immediately preceding method in the series (except the first method of the series in which the sample is the initial sample that contains all the proteins). The resolved proteins from the final electrophoretic method are then detected using various techniques.

The electrophoretic methods typically are capillary electrophoresis methods, such as capillary isoelectric focusing electrophoresis (CIEF), capillary zone electrophoresis (CZE) and capillary gel electrophoresis (CGE), although the methods are amenable to other capillary electrophoresis methods as well. The particular order of the methods can vary. Typically, the methods utilize combinations of electrophoretic methods which separate proteins on the basis of different characteristics (e.g., size, charge, isoelectric point).

In certain methods, the proteins are labeled to more easily detect the resolved proteins, to alter the charge of the proteins, to facilitate their separation, and/or to increase the signal-to-noise ratio. Labeling also enables certain methods to be conducted such that the resolved proteins obtained from the final electrophoretic method are quantitated. Quantitation allows the relative abundance of proteins within a sample, or within different samples, to be determined. In certain methods, the time at which proteins are labeled is selected to precede electrophoresis by capillary zone electrophoresis. By selectively labeling certain residues, resolution of proteins during capillary zone electrophoresis can be increased.

Resolution, quantitation and reproducibility are enhanced by utilizing a variety of techniques to control elution of proteins during an electrophoretic method. The particular elution technique employed depends in part upon the particular electrophoretic method. However, in general, hydrodynamic, salt mobilization, pH mobilization and electroosmotic flow are utilized to controllably elute resolved proteins at the end of each electrophoretic separation.

Some methods provide for additional analysis after the electrophoretic separation. The type of analysis can vary and include, for example, infra-red spectroscopy, nuclear magnetic resonance spectroscopy, UV/VIS spectroscopy, fluorescence spectroscopy, and complete or partial sequencing. In certain methods, proteins in the final fractions are further analyzed by mass spectroscopy to determine at least a partial sequence for each of the resolved proteins (i.e., to determine a protein sequence tag).

Thus, certain other methods involve performing one or more capillary electrophoretic methods, each of the one or more methods involving: (i) electrophoresing a sample containing multiple proteins within an electrophoretic medium contained within a capillary, and (ii) withdrawing and collecting multiple fractions, each fraction containing proteins resolved during the electrophoresing step. Each method in the series is conducted with a sample from a fraction collected in the preceding electrophoretic method, except the first electrophoretic method which is conducted with a sample containing the original mixture of proteins. The proteins are labeled prior to conducting the last electrophoretic method. Either the proteins in the initial sample are labeled (i.e., labeling precedes all the electrophoretic separations), or the proteins contained in fractions collected are labeled prior to the last electrophoretic method. The final electrophoretic method is performed, and resolved protein within, or withdrawn from, the capillary utilized to conduct the final method is detected with a detector. Hence, the detector is adapted to detect resolved protein within the capillary used in the final method or is connected in line with the capillary to detect resolved proteins as they elute from the capillary. In some instances, the detected proteins are quantitated and further analyzed by mass spectroscopy to determine their relative abundance and/or to establish a protein sequence tag for each resolved protein.

DETAILED DESCRIPTION

I. Overview

Figure 1:
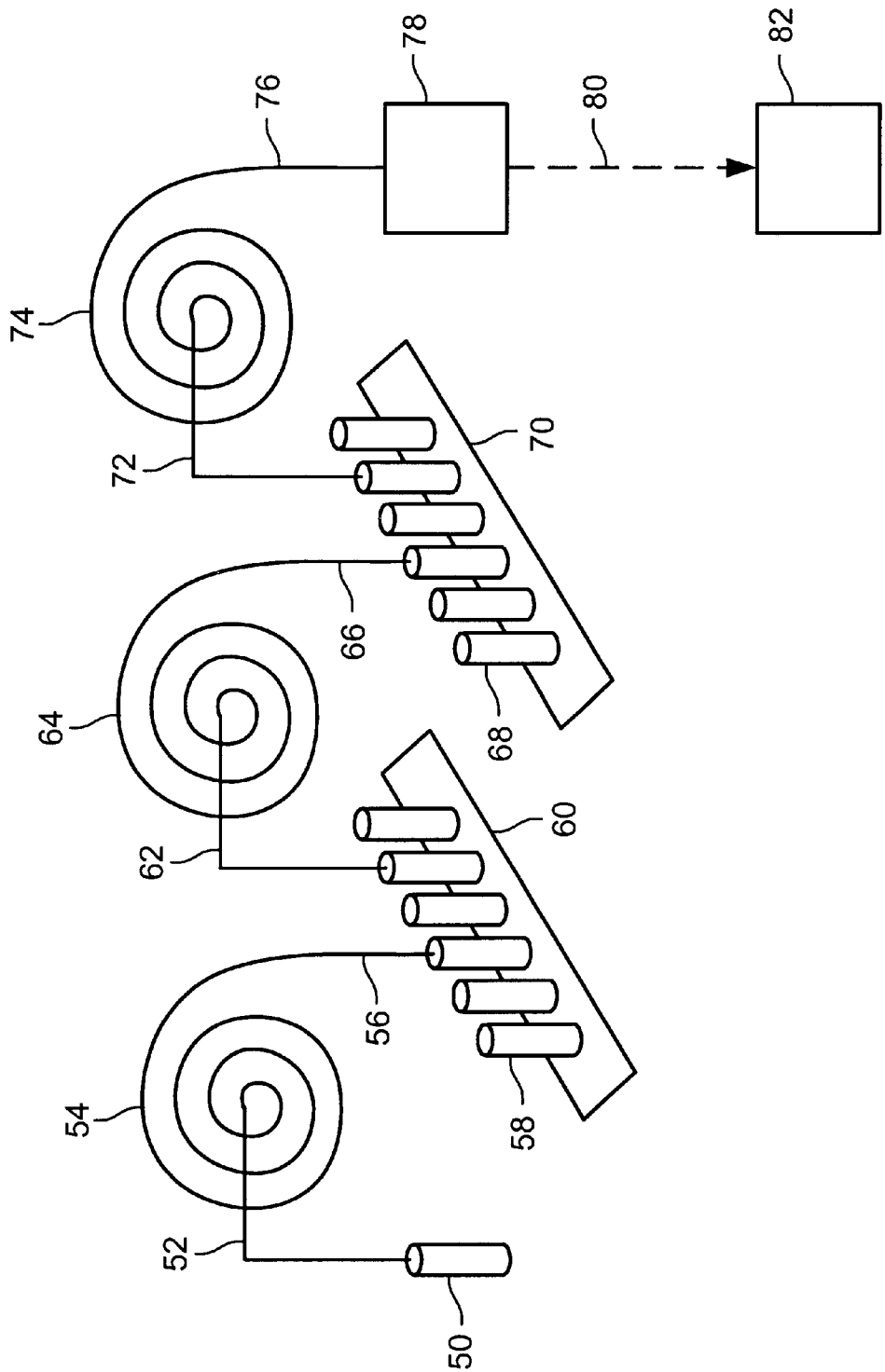
FIG. 1 is a schematic representation of one example of an electrophoretic system that can be utilized with certain methods of the invention.

The present invention provides methods and apparatus for achieving the separation of proteins, including significant resolution of proteins in complex mixtures from native cell and tissue samples. The invention is based in part upon the recognition that multidimensional electrophoretic methods involving multiple (typically different) electrophoretic methods performed in series utilizing controlled fractionation techniques to obtain defined fractions can be used to achieve high resolution of proteins. Labeling and detection steps can be included to increase sensitivity, alter the separation coordinates of the proteins, and to obtain accurate and reproducible quantitative information about the resolved proteins. Typically, the electrophoretic methods are capillary electrophoresis methods, particularly combinations of capillary isoelectric focusing (CIEF), capillary zone electrophoresis (CZE) and capillary gel electrophoresis (CGE).

Several features enable methods to be performed in a controlled and reproducible fashion. For example, once proteins have had an opportunity to fractionate within the electrophoretic medium contained within a capillary, elution conditions are tailored so that separated proteins are eluted in a controlled fashion to yield defined fractions in which the proteins contained within a fraction fall within a certain pH range, electrophoretic mobility range, or molecular weight range, for example. In certain methods, proteins are labeled at a selected stage of the separation process and the labeled proteins detected using a detector. Labeling enables proteins present at low concentration to more easily be detected and enhances reproducibility by increasing signal-to-noise ratios. The detector can be used to detect proteins as separated within an electrophoretic cavity or after they are eluted from the cavity. The combination of labeling and detection also enables separated proteins to be quantified. The combination of labeling and separation can alter the net charge or solubility of the proteins causing a change in their separation coordinates, for example, their separation order, the fraction in which they are collected, and elution time.

If additional information is desired, the methods can be expanded to include further analysis by techniques besides electrophoresis. For example, in certain methods, fractions collected from the final electrophoretic method are individually analyzed by mass spectroscopy to obtain additional information, such as molecular weight and partial sequence.

Quantitative detection and the ability to automate the methods means that the methods are amenable to a variety of screening, comparative and diagnostic studies. For example, the methods can be utilized to develop comparative protein expression data. Such comparative studies can be utilized to identify markers of specific diseases, potential targets for pharmaceuticals and/or drug candidates. Once markers that are selectively expressed in certain disease states, for example, are identified, the methods of the invention have utility in diagnostic applications. The methods of the invention can also be utilized to develop a protein database that includes, for example, separation coordinates, isoelectric points, apparent molecular weights and relative abundance information for proteins in different cells, tissues or states. The methods also find utility in studies on structure/activity relationships and in metabolic engineering investigations in which one genetically modifies a certain gene and then determines what effects such a modification has on cellular protein expression.

II. Separation Methods

A. General

The methods of the present invention utilize a combination of electrophoretic methods conducted in series to resolve mixtures of proteins. The methods are said to be conducted in series because the sample(s) electrophoresed in each method are from solutions or fractions containing proteins electrophoresed in the preceding method, with the exception of the sample electrophoresed in the initial electrophoretic method. As used herein, the terms protein, peptide and polypeptide are used interchangeably and refer to a polymer of amino acid residues. The term also applies to amino acid polymers in which one or more amino acids are chemical analogues of corresponding naturally-occurring amino acids, including amino acids which are modified by post-translational processes (e.g., glycosylation and phosphorylation).

The series of electrophoretic methods are typically conducted in such a way that proteins in an applied sample for each electrophoretic method of the series are isolated or resolved physically, temporally or spacially to form a plurality of fractions each of which include only a subset of proteins of the applied sample. Thus, a fraction refers to a protein or mixture of proteins that are resolved physically, temporally or spacially from other proteins in a sample subjected to electrophoresis. Resolved proteins can refer to a single species or a mixture of proteins that are separated from other proteins during an electrophoretic method. As just noted, samples in the various electrophoretic methods are obtained from such fractions, with the exception of the first electrophoretic method in which the sample is the original sample containing all the proteins to be separated.

Typically, these multiple electrophoretic methods in the series separate proteins according to different characteristics. For example, one method can separate proteins on the basis of isoelectric points (e.g., capillary isoelectric focusing electrophoresis), other methods can separate proteins on the basis of their intrinsic or induced (through the application of a label to certain ionizable amino acid residues) charge-to-mass ratio at any given pH (e.g., capillary zone electrophoresis), whereas other methods separate according to the size of the proteins (e.g., capillary gel electrophoresis). Such approaches that separate proteins through a series of electrophoretic methods are referred to herein as "multidimensional" electrophoretic methods, wherein each particular electrophoretic method constitutes a "dimension."

Figure 2A:
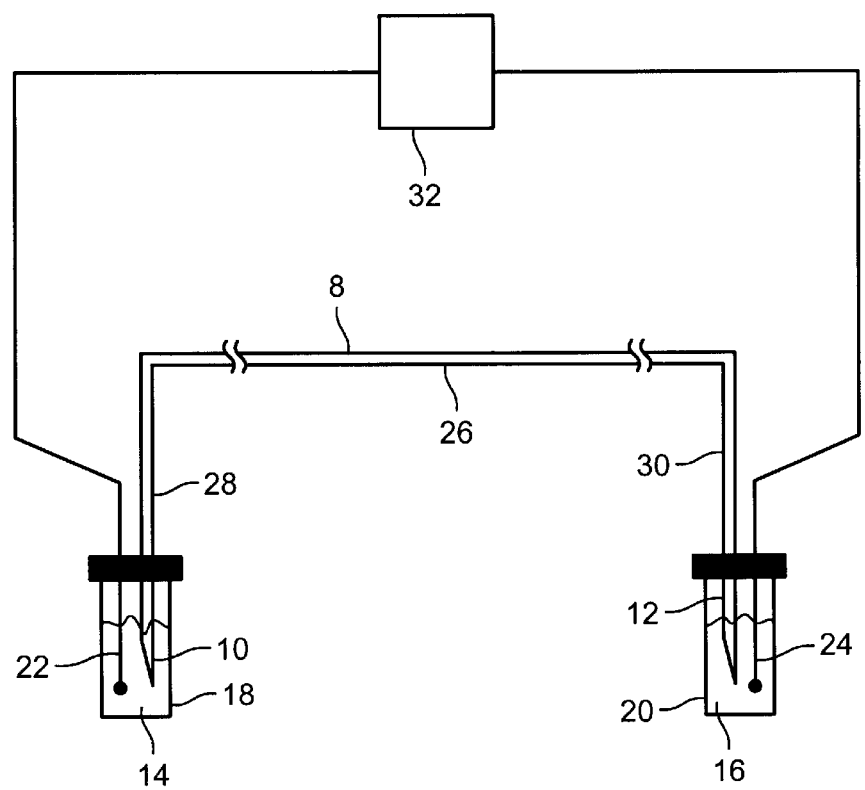
FIG. 2A is a schematic representation of some of the major elements of an electrophoretic system utilized in conducting certain electrophoretic methods of the invention.

Apparatus used to conduct various electrophoretic methods are known in the art. In general, however, and as shown in FIG. 2A, the basic configuration of a typical capillary electrophoretic system utilized in certain methods of the invention includes a capillary 8 having two ends 10, 12. One end 10 is in contact with an anode solution or anolyte 14 contained in an anode reservoir 18 and the other end 12 is in contact with a cathode solution or catholyte 16 in a cathode reservoir 20. One electrode (the anode) 22 is positioned to be in electrical communication with the anode solution 14 and a second electrode 24 is positioned to be in electrical communication with the cathode solution 16. The cavity 26 of the capillary 8 is filled with an electrophoretic medium, which in some instances can include a polymer matrix. As used herein, the term anode refers to the positively charged electrode. Thus, negatively charged species move through the electrophoretic medium toward the anode. The term cathode refers to the negatively charged electrode; positively charged species migrate toward this electrode. The anolyte is the solution in which the anode is immersed and the catholyte is the solution in which the cathode is immersed.

Sample is introduced into the capillary 8 via an inlet 28, and the protein components therein resolved as an electrical field is applied between the two electrodes 22, 24 by a power source 32 and the proteins separate within the electrophoretic medium contained within the separation cavity 26. Protein components can be controllably eluted from the capillary via outlet 30 by controlling various parameters such as electroosmotic flow (see infra) and/or by changing the composition of one or both of the reservoir solutions (e.g., adjusting the pH or salt concentration). Typically, the inlet 28 and the outlet 30 are simply portions of the capillary formed to allow facile insertion into a container containing sample, anolyte or catholyte.

The term "capillary" as used in reference to the electrophoretic device in which electrophoresis is carried out in the methods of the invention is used for the sake of convenience. The term should not be construed to limit the particular shape of the cavity or device in which electrophoresis is conducted. In particular, the cavity need not be cylindrical in shape. The term "capillary" as used herein with regard to any electrophoretic method includes other shapes wherein the internal dimensions between at least one set of opposing faces are approximately 2 to 1000 microns, and more typically 25 to 250 microns. An example of a non-tubular arrangement that can be used in certain methods of the invention is the a Hele-Shaw flow cell [67, 68]. Further, the capillary need not be linear; in some instances, the capillary is wound into a spiral configuration, for example.

An example of a system utilized with certain methods of the invention is illustrated in FIG. 1. This particular example shows a system in which three electrophoresis methods (initial, intermediate and final methods) are linked. The particular number of electrophoretic methods conducted can vary, although the methods of the invention include at least two electrophoretic methods. Most typically, the methods utilize two or three electrophoretic separation methods.

As can be seen in FIG. 1, an initial sample containing a plurality of proteins is introduced from sample container 50 into a first separation cavity of a first capillary 54 via sample inlet 52 utilizing any of a number of methods known in the art. Examples of suitable methods include, pulling sample into the sample inlet 52 under vacuum (e.g., by pulling a vacuum on the sample outlet) or pushing sample into the sample inlet 52 by pressurizing the sample container 50. Electromigration, often referred to as electrokinetic injection, is another option. Once the initial sample is introduced into sample inlet 52, the sample is then electrophoresed within the first separation cavity within the first capillary 54. The first separation cavity contains a desired electrophoretic medium in which proteins in the initial sample are at least partially resolved. Electrophoretic medium containing resolved proteins is withdrawn from the first cavity, typically out the end of the separation cavity opposite the end in which sample was introduced, although other withdrawal sites can be utilized (see infra). The withdrawn medium travels through outlet 56 and is collected in separate containers 58 as multiple fractions. As shown in FIG. 1B, the containers 58 into which fractions are collected are typically associated with a fraction collection device (a portion of which is shown 60) capable of automatically advancing a set of containers 58 to collect defined fractions (e.g., fractions of a certain volume or covering a selected pH range).

A sample from a fraction collected from the first electrophoretic method is then withdrawn from one of the plurality of containers 58, again utilizing techniques such as those described supra, via a second sample inlet 62. Proteins in the sample from the fraction can then be further resolved by conducting an intermediate electrophoretic method (in the example shown in FIG. 1, the second electrophoretic method). The sample is introduced into a second capillary 64 via inlet 62 and the proteins within the sample further separated within the electrophoretic medium contained within the second separation cavity of the second capillary 64 and then eluted from the cavity via outlet 66. As with the first electrophoretic separation, the electrophoretic medium containing the resolved or partially resolved proteins is collected as separate fractions within containers 68 typically aligned and advanced by a second fraction collection device (a portion of which is shown 70).

A process similar to the second/intermediate method is conducted during the final electrophoretic method (the third electrophoretic separation method shown in FIG. 1). Sample is drawn via inlet 72 from a container 68 containing a fraction obtained during the preceding method and is introduced into a third or final electrophoretic cavity of a third capillary 74 containing a third electrophoretic medium in which proteins contained in the applied sample are separated still further yet by electrophoresis. The third electrophoretic medium containing the further isolated proteins is subsequently withdrawn through outlet 76.

As noted above, more than the three electrophoretic methods shown in FIG. 1 can be performed. Such methods essentially involve repeating the general steps described for the second/intermediate electrophoretic separation above one or more times.

Following the final electrophoretic separation, a variety of different options for analyzing the resolved proteins are available. As shown in FIG. 1, withdrawn electrophoretic medium can be passed through a detector 78 in fluid communication with the separation cavity of the last capillary 74 to detect the resolved proteins. The detector 78, or an optional quantifying device capable of receiving a signal from the detector (not shown), can be used to quantitate the amount of protein within a certain portion or fraction of the electrophoretic medium.

Alternatively, or in addition, fractions can be taken from the electrophoretic medium exiting the final capillary 74 or the detector 78 and analyzed by an analyzer 82 using some technique other than electrophoresis. Examples of such techniques include various spectroscopic methods (e.g., IR, UV/VIS and NMR) and various mass spectroscopy methods (e.g., electrospray ionization-time of flight [ESI-TOF] mass spectroscopy). Mass spectral data, for example, can be utilized to deduce a partial or full sequence of the protein(s) (i.e., determine a protein sequence tag) within a particular fraction. FIG. 1 depicts a situation in which sample is withdrawn via line 80 (dashed to indicate optional nature of this step) to another analyzer 82 (e.g., mass spectrometer).

A number of other configurations can be utilized. For example, the capillaries and detector(s) can be fabricated within a microfluidic chip (see infra).

The specific elution conditions utilized to withdraw resolved proteins from the separation cavity depends upon the type of electrophoretic method conducted and is described more fully below for each of the electrophoretic methods typically utilized in the present invention. In general, however, once proteins have been resolved, the conditions within the separation cavity are adjusted as necessary (or the initial conditions selected) to achieve selective or controlled elution of the proteins from the cavity. For example, elution can be achieved by adding salts to, or adjusting the pH of, the anode or cathode solution, by regulating electroosmotic flow, by applying hydrodynamic pressure or combinations of the foregoing.

Using the methods of the invention, resolved proteins can be isolated physically (e.g., placement into different containers such as illustrated in FIG. 1), spatially (e.g., spread throughout the electrophoretic medium contained in the separation cavity) and/or temporally (e.g., controlling elution so different proteins within a sample elute from the capillary at different times). Thus, the methods of the invention can separate mixtures of proteins as a function of the composition of elution buffers and/or time, and are not limited to the spatial separation of proteins as are certain traditional two-dimensional (2-D) gel electrophoresis systems. Instead, with controlled elution, fractions can be collected so that proteins within a fraction fall within a range of isoelectric, electrophoretic mobility, or molecular weight values, for example. Controlled elution of proteins means that methods can be performed in a reproducible fashion. Such reproducibility is important in conducting comparative studies and in diagnostic applications, for example.

During the elution or withdrawing of resolved proteins, generally only a portion of the electrophoretic medium containing the resolved proteins is typically collected in any given fraction. This contrasts with certain 2-D methods in which a gel containing all the resolved proteins is exuded from the separation cavity and the exuded gel containing all the proteins is used to conduct another electrophoretic separation.

Spacially, physically or temporally resolved proteins obtained at the conclusion of one electrophoretic method are then used as the source of samples for further separation of proteins contained within the fraction during a subsequent electrophoretic method. As illustrated in FIG. 1, typically samples from different resolved fractions are sequentially electrophoresed on the same capillary. Normally another sample is not applied until the proteins in the preceding sample are sufficiently withdrawn from the separation cavity so that there is no overlap of proteins contained in different fractions. Sequential elution of fractions through the same column can significantly reduce or eliminate variations resulting from differences in cross-linking or electric field strength that can be problematic in certain slab gel electrophoretic methods. Hence, sequential separation can further enhance the reproducibility of the methods of the invention. Other methods, however, can be performed in a parallel format, wherein samples from different fractions are electrophoresed on separate capillaries. This approach allows for separations to be completed more quickly. However, the use of multiple capillaries can increase the variability in separation conditions, thereby reducing to some extent reproducibility between different samples.

In certain methods, proteins are labeled at a selected stage of the separation process and then detected using the detector. Labeling enables proteins present at low concentration to more easily be detected and enhances reproducibility by increasing signal-to-noise ratios. The detector can be used to detect proteins as separated within an electrophoretic cavity or after they are eluted from the cavity. The combination of labeling and detection also enables separated proteins to be quantified. The point in the overall method at which labeling is conducted depends in part on the particular electrophoretic methods being conducted as discussed more fully below. In general, however, labeling is typically conducted before a gel capillary electrophoretic separation is performed; whereas, labeling is normally conducted after capillary isoelectric focusing is performed rather than before. Labeling can also be used before a zone capillary electrophoresis separation is performed as a means to modify the net charge on the proteins and their relative electrophoretic mobilities.

As noted above, some of the more commonly used electrophoretic methods utilized in the present invention are capillary isoelectric focusing electrophoresis, capillary zone electrophoresis and capillary gel electrophoresis. Specific issues regarding the performance of these methods are described in the following sections.

B. Capillary Isoelectric Focusing Electrophoresis (CIEF)

1. General

Isoelectric focusing is an electrophoretic method in which zwitterionic substances such as proteins are separated on the basis of their isoelectric points (pI). The pI is the pH at which a zwitterionic species such as a protein has no net charge and therefore does not move when subjected to an electric field. In the present invention, proteins can be separated within a pH gradient generated using ampholytes or other amphoteric substances within an electric field. A cathode is located at the high pH side of the gradient and an anode is located at the low pH side of the gradient. Proteins introduced into the gradient focus within the pH gradient according to their isoelectric points and then remain there. General methods for conducting CIEF are described, for example, by Kilar, F., "Isoelectric Focusing in Capillaries," in *CRC Handbook on Capillary Electrophoresis: A Practical Approach*, CRC Press, Inc., chapter 4, pp. 95–109 (1994); and Schwartz, H., and T. Pritchett, "Separation of Proteins and Peptides by Capillary Electrophoresis: Application to Analytical Biotechnology," Part No. 266923 (Beckman-Coulter, Fullerton, Calif., 1994); Wehr, T., Rodriquez-Diaz, R., and Zhu, M., "Capillary Electrophoresis of Proteins," (Marcel Dekker, NY, 1999), which are incorporated herein by reference in their entirety.

2. System and Solutions

Because CIEF is primarily an equilibrium technique with low current densities, capillary heating typically is not a problem. Therefore, fairly large bore capillaries can be utilized. Suitable sizes include, but are not limited to, capillaries having internal diameters of 2–600 $\mu$m, although more typically capillaries having internal diameters of 25–250 $\mu$m are utilized. The use of relatively large bore capillaries means the method can use relatively high protein loads, which facilitates detection in the following dimension (s). This feature of CIEF makes the method well-suited for the initial or one of the early electrophoretic separations in the series. However, smaller diameter capillaries enable temperature to be controlled more carefully and, in some methods, result in improved signal detection (e.g., by laser induced fluorescence (LIF) detection of fluorescently labeled proteins).

The capillaries can have varying lengths. The length selected depends in part on factors such as the extent of separation required. Typically, the capillaries are about 10 to 100 cm in length, although somewhat shorter and longer capillaries can be used. While longer capillaries typically result in better separations and improved resolution of protein mixtures, longer capillaries also afford more opportunities for protein-wall interactions and lower field strength. Consequently, there tends to be an upper limit on capillary length beyond which resolution may be lost. Longer capillaries can be of particular use in resolving low abundance proteins. Further guidance on size and length of capillaries is set forth, for example, in Palmieri, R. and J. A. Nolan, "Protein capillary electrophoresis: Theoretical and experimental considerations for methods development," in: CRC Handbook of Capillary Electrophoresis: A Practical Approach, Chp. 13, pgs. 325–368 (CRC Press, Boca Raton, 1994).

Generally, the capillaries are composed of fused silica, although plastic capillaries and PYREX (i.e., amorphous glass) can be utilized in certain methods. As noted above, the capillaries do not need to have a round or tubular shape. Other shapes wherein the internal dimension between opposing faces is within the general range set forth in this section can also be utilized.

A variety of different anode and cathode solutions can be used. Common solutions include sodium hydroxide as the catholyte and phosphoric acid as the anolyte. Similarly, a number of different ampholytes can be utilized to generate the pH gradient, including numerous commercially available ampholyte solutions (e.g., BioLyte, Pharmalyte and Servalyte). The selection of ampholytes and the breadth of the ampholyte gradient can impact the resolution that is achieved by CIEF methods. Narrow ampholyte gradients increase the number of theoretical plates in the separation and can be beneficial for higher resolution separations over narrow pI ranges.

CIEF methods utilized in the separations of the invention can be conducted in capillaries containing polymeric matrices or in free solution (i.e., no gel or other polymeric matrix). Polymer matrices are typically added to slow electroosmotic flow; however, in some instances, inclusion of polymeric matrices can restrict movement of larger proteins (see, e.g., Patton, 26). The use of free solutions is preferable in such cases possibly in combination with other methods (e.g., capillary coatings, gel plugs, or induced electric fields) to control the electroosmotic flow.

3. Sample Preparation

Typically protein samples to be electrophoresed by CIEF are denatured prior to loading the sample into the capillary. This ensures that the same proteins all have the same charge and thus identical proteins focus at the same location rather than potentially at multiple zones within the capillary. Denaturants (e.g., urea), non- and zwitterionic-surfactants (e.g., IGEPAL CA-630 or 3-[{3-cholamidopropyl}dimethylammonio]-1-propane sulfonate) can also be used to suppress protein-wall and/or protein-protein interactions that can result in protein precipitation. Another advantage of denaturing the proteins prior to electrophoresis is that the results can be used in comparisons with archival data typically obtained under denaturing conditions.

A typical denaturing buffer includes urea and a nonionic or zwitterionic surfactant as denaturants; a reducing agent (e.g., dithiothreitol (DTT) or mercaptoethanol) is typically included to reduce any disulfide bonds present in the proteins. Other denaturants besides urea that can be used include, but are not limited to, thiourea and dimethylformamide (DMF). Generally, guanidine hydrochloride is not utilized as a denaturant because of the very high ionic strength it imparts to a sample. Exemplary neutral detergents include polyoxyethylene ethers ("tritons"), such as nonaethylene glycol octylcyclohexyl ether ("TRITON" X-100), polyglycol ethers, particularly polyalkylene alkyl phenyl ethers, such as nonaethylene glycol octylphenyl ether ("NONIDET" P-40 or IGEPAL CA-630), polyoxyethylene sorbitan esters, such as polyoxyethylene sorbitan monolaurate ("TWEEN"-20), polyoxyethylene ethers, such as polyoxyethylene lauryl ether ($C_{12}E_{23}$) ("BRIJ"-35), polyoxyethylene esters, such as 21 stearyl ether ($C_{18}E_{23}$) ("BRIJ"721), N,N-bis[3-gluconamido-propyl]cholamide ("BIGCHAP"), decanoyl-N-methylglucamide, glucosides such as octylglucoside, 3-[{3-cholamidopropyl}dimethylammonio]-1-propane sulfonate and the like.

The optimal amount of denaturant and detergent depends on the particular detergent used. In general the denaturing sample buffers contain up to 10 M urea (more typically 4–8 M and most typically 6–8 M). Specific examples of suitable buffers (and denaturants and nonionic surfactants for inclusion therein) include those described by Hochstrasser et al.[5] and O'Farrell[6]. Denaturation is typically advanced by heating for 10 min at 95 ° C. prior to injection into the capillary. Adjustments in the denaturing sample buffers are made as necessary to account for any electroosmotic flow or heating effects that occur (see, e.g., Kilar, F., "Isoelectric Focusing in Capillaries," in *CRC Handbook on Capillary Electrophoresis: A Practical Approach*, CRC Press, Inc., chapter 4, pp. 95–109 (1994)).

The amount of protein within a sample can vary and, as noted above, depends in part of the size of the capillary used. In general, the capillary is loaded with 0.1 to 5.0 mg of total protein. Samples can be spiked with one or more known pI standards to assess the performance of the method.

4. Elution

A variety of techniques can be utilized to elute or withdraw electrophoretic medium containing resolved proteins out from the capillary, but these methods fall into three general categories: hydrodynamic elution, electroelution and control of electroosmotic flow.

a. Hydrodynamic/Pressure Elution

Hydrodynamic or pressure elution involves applying pressure (or pulling a vacuum) via an appropriate pump connected with one end of the capillary (see, e.g. Kilar, F., "Isoelectric Focusing in Capillaries," in *CRC Handbook on Capillary Electrophoresis: A Practical Approach*, CRC Press, Inc., chapter 4, pp. 95–109 (1994)). However, hydrodynamic elution can cause band broadening and loss of resolution due to the parabolic flow profile that is formed in the capillary.

b. Electroelution

Electroelution, the other major approach, encompasses a variety of techniques and in general involves altering the solution at the anode and/or cathode to change some parameter (e.g., pH, ionic strength, salt concentration) of the electrophoretic medium in the separation cavity sufficiently to effect elution.

i. Salt Mobilization

One electroelution approach involves addition of a salt to the catholyte or anolyte, the salt having a non-acidic or non-basic counterion of the same charge as the acidic or basic species within the reservoir to which the salt is added so that the counterion migrates from the reservoir into the capillary. Since electrical neutrality must be maintained within the capillary, the movement of the counterion into the capillary results in a reduction of the concentration of protons or hydroxide within the capillary, and thus the pH is either raised or lowered. The theoretical basis for this type of mobilization is described by S. Hjerten, J.-L. Liao, and K.

Yao, J. Chromatogr., 387: 127 (1987). For example, if the catholyte is sodium hydroxide (i.e., the basic species is hydroxide) then a salt having a negatively charged counterion other than hydroxide is added, for example sodium chloride. Movement of chloride ion into the capillary reduces the local concentration of hydroxide within the capillary, thereby decreasing the pH. As another example, if the anolyte is phosphoric acid, then a salt having a counterion other than a proton is added, for example sodium phosphate. In this instance, movement of sodium ion into the capillary reduces the local concentration of protons within the capillary thereby increasing the pH. As the pH is lowered or raised within regions of the capillary due to the presence of the added counterion, elution occurs since the ampholytes, and the focused proteins, migrate to the newly-defined pH regions corresponding to their isoelectric points. It has been shown that both the type and concentration of salt used for mobilization has impact on the resolution of eluted protein peaks [R. Rodriguez-Diaz, M. Zhu, and T. Wehr, J. Chromatogr. A, 772:145 (1997)]. In particular, the addition of sodium tetraborate instead of sodium chloride to the catholyte results in greatly increased resolution of separated proteins.

ii. pH Mobilization

Another technique, referred to herein as "pH mobilization" can also be utilized to elute proteins during CIEF. In this approach, an additive is added to either the anode or cathode solution to alter the pH of the solution. Unlike salt mobilization, however, the additive does not contribute a mobile counterion that moves into the capillary. Here, the elution occurs as a result of the pH gradient being redefined by the pH of one or both of the reservoirs; therefore, proteins with pI's that fall outside of this redefined pH gradient are eluted into either the anode or cathode reservoirs. Typically, the technique for cathodic mobilization would proceed as follows. Once the proteins are focused in an exemplary pI range of 3–10 using phosphoric acid as the anolyte and sodium hydroxide as the catholyte, the cathodic capillary end is immersed into a reservoir containing a solution that has a pH slightly less than 10, for example 50 mM imidazole (pKa 7) which has a pH of 9.85. The proteins are then allowed to refocus in the capillary, recognizable by a stabilization of the current through the capillary, the pI range now being defined by 3–9.85. Any proteins with an isoelectric point of 9.85 to 10 are eluted into the catholyte. The process can be repeated with catholyte containing a species that reduces the pH to slightly less than 9.85. In a stepwise fashion, the pH can be continued to be reduced to pH 7, thereby collecting separated proteins in fractions that span the range of 7–10. At this point, anodic mobilization can proceed by replacing the anolyte with acids of increasing pKa to selectively increase the pH from 3 to 7, thereby collecting fractions in the acidic range (pH 3–7). The number of fractions can vary depending on the desired fractionation resolution. Typically, these fractions are defined by differences of 0.05–0.5 pH units.

The technique of pH mobilization can be useful for protein samples containing a high concentration of one or more proteins that may cause uneven spatial gradients inside the capillary. Using pH mobilization, only those proteins with isoelectric points below or above the pI range that is defined by the reservoir pH's are eluted. This elution would, therefore, be reproducible regardless of differences in the shape of the capillary pH gradient or the presence of uneven spatial gradients inside the capillary.

C. Electroosmotic Flow (EOF)

Regulating the magnitude of electroosmotic flow (EOF) significantly affects the preceding electroelution methods (see supra) and is another means by which resolved proteins can be selectively withdrawn upon conclusion of an isoelectric focusing separation. EOF is generated by the ionization of silanol functionalities on the surface of a silica capillary. Such ionization results in a layer of protons in the electrophoretic medium at the surface of the silica capillary. Once an electric field is applied, the layer of protons essentially constitutes a positively charged column of fluid which migrates toward the cathode, thereby causing bulk flow of the electrophoretic medium within the capillary. Apparent velocity of analytes is equal to the sum of the electroosmotic flow and their electrophoretic mobility. Thus, by controlling EOF, one can control or regulate the rate at which proteins move through the capillary. In CIEF methods, generally EOF should be controlled to allow proteins within an injected sample sufficient time to focus before the proteins begin eluting from the capillary.

A variety of techniques can be utilized to regulate EOF. One approach involves coating the walls of capillaries with various agents. For example, EOF along glass silicate surfaces can be substantially reduced by silanizing them with a neutral silane reagent that masks a substantial percentage of surface silanol groups (e.g., polyacrylamide, polyethylene glycol and polyethylene oxide). The magnitude of EOF can be further controlled by using silanizing reagents that include positively or negatively charged groups. Positively charged coatings can be used to nullify surface negative charges to give a net surface charge of zero, so that EOF approaches zero. Coatings with higher positive charge densities can be used to reverse the direction of EOF for charged surface materials. This can be useful for slowing the net migration rates of positively charged sample species. Conversely, negatively charged coatings can be used to impart to or increase the magnitude of the negative charge on surfaces, so as to increase the net migration rates of negatively charged species. Representative positively charged coatings include trialkoxysilanes with polyethyleneimine, quaternized polyethyleneimine, poly(N-ethylaminoacrylamide) and chitosans, for example. Representative negatively charged coatings include trialkoxysilanes with carboxylate and sulfonate containing materials such as poly(methylglutamate) and 2-acrylamido-2-methylpropanesulfonate polymers, for example. It will be recognized that charged coatings can also effectively reduce sample adsorption, especially for samples having the same charge polarity as the coating.

The separation medium can also include soluble agents for dynamically coating the walls of the separation cavity, to help reduce EOF during electrophoresis. Such soluble coating agents include quaternary ammonium-containing polymers, methyl cellulose derivatives, cellulose acetate, polyethylene oxide, chitosan, polyvinyl alcohol, polyethylene glycol, polyethylenimine, and polyethylene oxide-polypropylene oxide-polyethylene oxide triblock copolymers, for example. Typically, soluble coating agents are included at concentrations of about 0.05% to about 4%, and more typically of about 1% to about 2%.

EOF and sample absorption can also be adjusted by including suitable reagents in the separation medium and running buffers. For example, negative surface charges can be masked by including a cationic additive in the medium, such as metal amine complexes, amines and polyamines such as propylamine, triethylamine, tripropylamine, triethanolamine, putrescine, spermine, 1,3-diaminopropane, morpholine, and the like. Zwitterionic species comprising both negatively and positively charged groups that are isoelectric at the pH of electrophoresis can also be used, such as trialkylammonium propyl sulfonates, where alkyl is methyl, ethyl, propyl, and longer alkyl chains.

Another approach involves the generation of a current that opposes EOF. Typically, this is accomplished by applying a thin film of metal (e.g., iridium tin oxide or copper) to an external surface of the capillary. Application of current to the film generates a relatively small induced current within the capillary to reverse the EOF (see, e.g., Schasfoort, R. B. M., Schlautmann, S., Hendrikse, J., and van den Berg, A., "Field-Effect Flow Control for Microfabricated Fluidic Networks," Science, 286:942–945 (1999)).

Figure 2B:
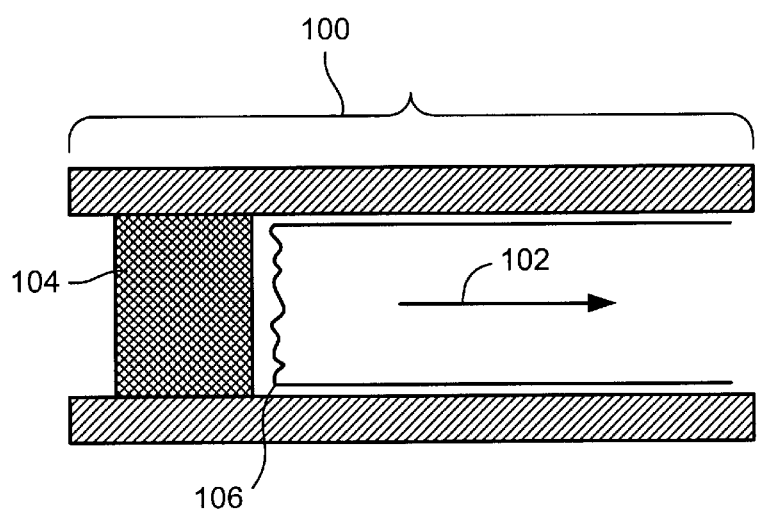
FIG. 2B is a cross-sectional view of a capillary showing the orientation of a porous plug inserted into the capillary to control electroosmotic flow in certain methods of the invention.

Placing a porous plug at a location upstream from where sample is introduced (upstream referring to a direction opposite the flow of proteins through the capillary) can also be utilized to control EOF. An example illustrating the location of the plug is illustrated in FIG. 2B where the capillary 100 extends from the anode reservoir (not shown) at one end and the cathode reservoir at the other end (not shown). Protein migration is in the direction of arrow 102 (i.e., from the anode to cathode direction). As can be seen, the porous plug 104 is positioned to be upstream of the trailing edge 106 of the sample once introduced into the capillary 100. The porous plug 104 is typically formed of a polymeric material and remains relatively stationary during electrophoretic runs. Examples of suitable materials from which the plug can be formed include polymerized acrylamide with diacrylamide crosslinkers and agarose. Although not intending to be bound by any particular theory, the porous plug 104 appears to function as a momentum transfer barrier by blocking replacement of bulk fluid that in the absence of the plug 104 would move toward the cathode reservoir.

In some methods, such as those containing large amounts of protein and/or a large number of different proteins, EOF should be reduced to very low levels to allow proteins the opportunity to focus before the electrophoretic medium begins eluting from the capillary due to EOF. In certain methods an EOF of less than or equal to $0.5\times10^{-6}$ cm$^2$/V-s (at pH 8.6, and 25 mM TRIS-phosphate) has been found to allow ample time for the necessary focusing of proteins before sample elutes from the capillary. Methods described above can reduce EOFs to these levels.

Thus, the foregoing approaches enable fractions to be collected according to different criteria. Electroelution techniques, for example, can be used to collect fractions having a defined pH range. EOF elution and pressure elution, in contrast, can be used to separate fractions according to time of elution. Other techniques can also be utilized to elute resolved proteins after CIEF (see, e.g. Kilar, F., "Isoelectric Focusing in Capillaries," in CRC Handbook or Capillary Electrophoresis: A Practical Approach, CRC Press, Inc., chapter 4, pp. 95–109 (1994)). The controlled elution techniques are useful for enhancing reproducibility, an important factor in comparative and diagnostic methods. Such techniques also provide improved tolerance of high abundance proteins as compared to methods relying on spatial separation.

C. Capillary Zone Electrophoresis (CZE)

1. General

Capillary zone electrophoresis is an electrophoretic method conducted in free solution without a gel matrix and results in the separation of molecules such as proteins based upon their intrinsic charge-to-mass ratio. One advantage to CZE methods is the ability to run with solvent systems that would normally be incompatible with typical water soluble gel matrices. Nonaqueous or water miscible solvent systems can be used to improve the solubility of hydrophobic and membrane bound proteins that would normally not be resolved by gel electrophoretic methods. General methods for conducting the method are described, for example, by McCormick, R. M. "Capillary Zone Electrophoresis of Peptides," in CRC Handbook of Capillary Electrophoresis. A Practical Approach, CRC Press Inc., chapter 12, pp. 287–323 (1994); Jorgenson, J. W. and Lukacs, K. D., J. High Resolut. Chromatogr. Commun., 4:230 (1981); and Jorgenson, J. W. and Lukacs, K. D., Anal. Chem. 53:1298 (1981)), each of which is incorporated by reference in its entirety.

2. System and Solutions

In general, the capillaries described above for CIEF are also suitable for conducting CZE methods. Often the capillaries have internal diameters of about 50 to 100 microns. Buffer composition and pH can significantly influence separations since separations in CZE are based upon charge-to-mass ratios and the charge of a protein is dependent upon the pH of the surrounding solution. At the extremes of pH (i.e., below 2 and above 10) it is typically difficult to achieve resolution of proteins because all residues are either fully protonated or deprotonated and many proteins have a similar number of acidic and basic residues per unit mass. Selectivity is typically enhanced at intermediate pH. For proteins having a relatively high percentage of acidic residues, selectivity can often be enhanced near pH 4.5. For those proteins having a high concentration of basic residues, selectivity can be enhanced near pH 10.

In CZE, solutions at the anode and cathode are typically the same. The buffer utilized can be essentially any buffer, the choice of buffer being controlled in part by the pH range at which the electrophoretic method is conducted and its influence on the detector noise. Examples of useful buffers at low pH include, but are not limited to, phosphate and citrate; useful buffers at high pH include Tris/Tricine, borate and CAPS (3-(cyclohexylamino)-1-propane sulfonic acid). Further guidance regarding suitable buffers and buffer additives is described by McCormick, R. M. "Capillary Zone Electrophoresis of Peptides," in CRC Handbook of Capillary Electrophoresis. A Practical Approach, CRC Press Inc., chapter 12 , pp. 287–323 (1994).

3. Elution

Elution can be accomplished utilizing some of the same methods described above for CIEF, namely pressure and EOF. As with CIEF, controlling EOF can be important in certain methods to prevent electrophoretic medium containing protein from eluting from the capillary before the proteins within the loaded sample have had an opportunity to separate. EOF can be controlled using the same methods utilized for controlling EOF in CIEF methods (e.g., coating the internal walls of the capillary, using a porous plug and generating an induced field to counteract EOF). Regulating and carefully selecting the pH and ionic strength of the electrophoretic medium is another technique that can be used. Because EOF results from ionization of the silanol groups on the interior capillary surface, by conducting CZE at relatively low pH (e.g., pH 2–5, more typically about pH 3–4) the number of silanol groups that are ionized is reduced. Such a reduction reduces EOF. To prevent sample elution prior to complete separation, in certain analyses the EOF should be reduced to <$1\times10^{-4}$ cm$^2$/V-s (at pH 8.6 and 25 mM TRIS-phosphate buffer). EOFs of this level can be obtained using the methods just described.

Another approach that is described more fully below in the detection and labeling section is to label proteins in the sample prior to injecting the sample containing the protein into the capillary. By selecting labels that preferentially react with certain functional groups such as amino or carboxyl groups, the charge-to-mass ratio of certain proteins can be altered. Such alterations can improve the resolution of proteins during electrophoresis as well as improve their detectability. (See Examples 1 and 2 below).

D. Capillary Gel Electrophoresis (CGE)

1. General

Capillary gel electrophoresis refers to separations of proteins accomplished by sieving through a gel matrix, resulting in the separation of proteins by size. In one format, proteins are denatured with sodium dodecyl sulfate (SDS) so that the mass-to-charge ratio is determined by this anionic surfactant rather than the intrinsic mass-to-charge ratio of the protein [50, 2]. This means that proteins can be separated solely on the basis of size without charge factoring into the degree of separation. The application of general SDS PAGE electrophoresis methods to capillary electrophoresis (CGE) is described, for example, by Hjertén, S., "Free zone electrophoresis," *Chromatogr. Rev.,* 9:122 (1967).

2. System and Solutions

The type of capillaries and their size are generally as described above for CZE. A variety of different buffers can be used, including commercially available buffers such as the "eCAP SDS" buffers manufactured by Beckman (see, also, 51, 30, 9 and 5). Various buffer additives can be utilized to increase resolution. Such additives, include, but are not limited to, small amounts of organic solvents, such as N,N-dimethylformamide, cyclohexyldiethylamine, dimethoxytetraethylene glycol and other polyols (e.g., ethylene glycol and polyethylene glycol) (see, e.g., [2] and [3]). The use of such solvents can improve the solubility of proteins in aqueous solution and enhance protein stability against thermal denaturation, [52] depress the electroosmotic flow in CZE and CGE [53], alter the electrical double-layer thickness at the capillary wall to inhibit protein binding interactions [47] and increase the viscosity of the running buffer which depresses the electroosmotic flow. Solvents utilized should be compatible with the polymer matrix inside the capillary.

Isotachophoresis (IPE) can be used in certain methods to increase resolution of proteins. For a general discussion of IPE, see, for example, B. J. Wanders and Everaerts, F. M., "Isotachophoresis in Capillary Electrophoresis," in *CRC Handbook of Capillary Electrophoresis: A Practical Approach,* chap. 5, pp. 111–127 (1994), which is incorporated by reference in its entirety. The velocity of a charged molecule moving through a capillary under a constant field strength depends on its relative mobility, which is a function of the mass/charge of the molecule, temperature, and viscosity of the medium through which it is moving. However, in the absence of an adequate concentration of highly mobile ions upstream of the sample ions, all the ions eventually have to migrate at the speed of the slowest ion once the electric field reaches a steady-state inside the capillary. This condition causes the anions to stack in order of their relative mobilities at the interface of the leading and terminating buffers.

Under SDS denaturing conditions, all the proteins present in the sample have nearly identical mass/charges. By using a higher mass/charge anion in the terminal buffer, one can force the proteins to move at a constant slow speed through the capillary. This has two effects. First, proteins "stack" at the terminal edge of the leading buffer increasing their effective concentration inside the capillary. Second, any separation between proteins is based on their size. Therefore, the use of a hybrid IPE-CGE method in which the IPE is used for sample "stacking" can improve the resolution possible in the subsequent CGE separation in some methods.

Various terminal buffer systems can be utilized in conjunction with IPE methods. In one system, ε-aminocaproic acid (EACA) is used as the terminal electrolyte because it has a high mass/charge at high pH (>6). Tris(hydroxyethyl) aminomethane (TRIS) citrate at 0.05M is used as the leading buffer at pH=4.8 and as an intermediate stacking buffer at pH=6.5. The sample proteins initially "stack" because EACA has a very low mobility in the pH 6.5 stacking buffer, but once the protein "stack" and EACA reach the lower pH leading buffer, the mobility of the EACA surpasses that of the proteins and separation commences (see, e.g., [57]). This system can be used to create a hybrid single column IPE-CPAGE system.

A 2 buffer system for IPE for the separation of proteins involves dissolving sample in 0.01M acetic acid, which is also used as the terminal electrolyte. The leading and background buffer was 0.02M triethylamine-acetic acid solution at pH 4.4. The sample in terminal buffer is sandwiched between the leading and background buffer. IPE continues until the background buffer overtakes the leading edge of the terminal buffer, at which point IPE stops and separation begins (see, e.g., [58]).

Another IPE approach that can be accomplished with any running buffer is to dissolve the sample in the running buffer but diluted to a lower ionic strength. This causes an increase in the electrical resistance in the capillary where the sample plug is loaded and correspondingly faster movement of the ions present in the sample matrix to running buffer boundary. The optimal ionic strength difference between the sample matrix and the running buffer is typically about 10-fold (see, e.g., [43]).

3. Elution

In general, the discussion of elution for CZE applies to CGE. Elution can be accomplished utilizing pressure and EOF. As with CIEF and CZE, controlling EOF can be important in certain methods to prevent electrophoretic medium containing protein from eluting before the proteins within the applied sample have had an opportunity to separate. The methods described supra for CIEF and CZE can be used to control EOF at desired levels. To prevent sample elution prior to complete separation, in certain analyses the EOF should be reduced to $<1\times10^{-4}$ cm$^2$/V-s (at pH 8.6 and 25 mM TRIS-phosphate buffer). EOF can be reduced to this range, for example, by controlling the pH of the buffer, by generation of a counteracting induced field, capillary coatings and a porous gel plug.

E. Labeling and Detection

As indicated in FIG. 1, electrophoretic solution withdrawn during the final electrophoretic separation can be directed toward a detector for the detection and quantitation of protein. This arrangement provides considerable flexibility with regard to the nature of detection and does not limit the methods to the standard gel staining detection techniques common in traditional 2-D gel electrophoresis analysis. The detector need not be positioned to detect eluted proteins as shown in FIG. 1, however. In other arrangements, the detector is adapted so that it can scan resolved proteins within the separation cavity of the capillary tube itself. To further enhance detection sensitivity, quantitation and reproducibility, proteins are labeled at some point prior to detection in certain methods. Depending upon the particular label used, signal-to-noise ratios can be achieved which permit the detection of low abundance proteins.

Although FIG. 1 depicts a single detector, additional detectors can be positioned to detect proteins eluting from all or at least multiple capillaries utilized in the different electrophoretic methods. One suitable arrangement, for example, involves utilizing a UV/VIS detector to detect eluting proteins from early and/or intermediate methods, in part to monitor the amount of protein being collected within a fraction. Labeling can then be conducted immediately prior to the final step with subsequent detection of labeled protein from the final capillary. If labeling is conducted at some earlier stage, then a detector (or detectors), can detect labeled protein after all subsequent electrophoretic methods in the series.

Proteins can be detected utilizing a variety of methods. One approach is to detect proteins using a UV/VIS spectrometer to detect the natural absorbance by proteins at certain wavelengths (e.g., 214 or 280 nm). In other approaches, proteins in the various fractions can be covalently labeled through a variety of known methods with chromagenic, fluorophoric, or radioisotopic labels. A wide variety of chemical constituents can be used to attach suitable labels to proteins. Chemistries that react with the primary amino groups in proteins (including the N-terminus) include: aryl fluorides [69, 70, 71, 72], sulfonyl chlorides [73], cyanates [74], isothiocyanates [75], immidoesters [76], N-hydroxysuccinimidyl esters [77], chlorocarbonates [78], carbonylazides [78], and aldehydes [79, 80]. Examples of chemical constituents that preferentially react with the carboxyl groups of proteins are benzyl halides [78, 81, 82] and carbodiimide [83], particularly if stabilized using N-hydroxysuccinimide [84]. Both of these carboxyl labeling approaches are expected to label carboxyl containing amino acid residues (e.g., aspartate and glutamate) along with that of the C-terminus. In addition, tyrosine residues can be selectively [$^{135}$I]-iodinated to allow radiochemical detection.

As alluded to supra, labeling can be performed at different points prior to detection. In general, however, the decision when to label proteins during the overall analysis depends on the particular CE methods utilized in the series. For example, if CIEF is utilized in one of the dimensions, then proteins are typically labeled after CIEF. Labeling can alter the pI of the proteins, thereby changing the locations at which the proteins focus during CIEF. This is not inherently problematic, but it means that the results cannot be compared with typical archival 2-D gel electrophoresis results that include an IEF dimension. Thus, to allow comparison with results obtained using more traditional approaches, it can be advantageous to delay labeling until after CIEF. Certain labels, however, can be utilized that have a minimal effect on the IEF pattern (see, e.g., U.S. Pat. No. 5,320,727, and Jackson, P. et al., *Electrophoresis*, 9:330–339 (1998), both of which are incorporated by reference in their entirety).

If the decision is made not to label protein prior to conducting CIEF for the foregoing reasons, proteins eluting from the CIEF capillary or proteins in collected fractions can nonetheless be detected by detecting UV absorbance or intrinsic fluorescence of the aromatic amino acids (e.g., tryptophan, phenylalanine and tyrosine). If, however, proteins are labeled prior to CIEF, any effect of pH on the absorptivity of the dye or fluorophor label can be mitigated by spin dialysis and buffer exchange to a constant pH before measurement, or by resuspending a constant collected volume into a higher ionic strength buffer of a constant pH.

Whereas labeling is generally conducted after the CIEF dimension to avoid altering isoelectric focusing patterns, there can be advantages to labeling proteins prior to a CZE dimension. Depending upon the composition of the protein-containing sample, labeling of proteins can affect the charge-to-mass ratio of the labeled proteins. For protein mixtures wherein the proteins have similar charge-to-mass ratios, the use of labels that preferentially react with particular residues can alter the charge-to-mass ratios sufficiently such that enhanced resolution is achieved. For example, a group of proteins can initially have a similar charge-to-mass ratio. However, if the proteins within the group are labeled with a neutral label that reacts primarily with lysine groups, proteins having a high number of lysine groups will bear more label and have a greater alteration in the charge-to-mass ratio than proteins having a lower number of lysine residues. This differential effect can translate into enhanced fractionation during electrophoresis. (See Examples 1 and 2).

A variety of labels that preferentially react with specific residues are available for use. The reactive functionality on the label is selected to ensure labeling of most or all of the components of interest. For example, sulfophenylisothiocyanate can be used to selectively label lysine residues [20], altering their charge from positive (below a pH of 10) to negative (above a pH of 0.5). Similarly, phenylisothiocyanate can be used to neutralize the lysine and N-terminal positive charges at all pH. Dansyl chloride can be used to lower the pH at which lysine and N-terminal residues carry a net positive charge. The addition of amino functional alkyl ammonium salts to aspartic and glutamic acid residues, such as through carbodiimide coupling, alters their charge from negative to positive at low pH.

There is somewhat greater flexibility in the time at which proteins are labeled relative to CGE. In some instances, pre-labeling is advantageous in that the separation can be viewed as it occurs and in that detection can be performed at the end without further labeling. With pre-labeling there are also fewer fractions of proteins to label. Pre-labeling methods for 1D-PAGE are described, for example, by Hames, B. D. in *Gel Electrophoresis of Proteins. A Practical Approach*, (Hames, B. D. and Rickwood, P., Eds.) $2^{nd}$ ed., pp.67–68, Oxford University Press, Oxford (1990) and Rose, D. R. J. and J. W. Jorgensen, "Post-capillary fluorescence detection in capillary zone electrophoresis using o-phthaldialdehyde," *J. Chromatogr.*, 447:117 (1988), which are incorporated by reference in their entirety.

Although certain types of labels are preferred to enhance separation in CZE methods, in general the label utilized during labeling in one of the methods of the invention can be quite diverse. In general the label should not interfere with fractionation during electrophoresis and should emit a strong signal so that even low abundance proteins can be detected. The label preferably also permits facile attachment to proteins. Suitable labels include, for example, radiolabels, chromophores, fluorophores, electron dense agents, NMR spin labels, a chemical tag suitable for detection in a mass spectrometer, or agents detectable by infrared spectroscopy or NMR spectroscopy for example. Radiolabels, particularly for spacially resolved proteins, can be detected using phosphor imagers and photochemical techniques.

Certain methods utilize fluorophores since various commercial detectors for detecting fluorescence from labeled proteins are available. A variety of fluorescent molecules can be used as labels including, for example, fluorescein and fluorescein derivatives, rhodamine and rhodamine derivatives, naphythylamine and naphthylamine derivatives, benzamidizoles, ethidiums, propidiums, anthracyclines, mithramycins, acridines, actinomycins, merocyanines, coumarins, pyrenes, chrysenes, stilbenes, anthracenes, naphthalenes, salicyclic acids, benz-2-oxa-1-diazoles (also called benzofurazans), fluorescamines and bodipy dyes. Specific examples of suitable fluorescent labels are listed in Table 1 below. A variety of appropriate fluorescent dyes are commercially available from Sigma Chemical Co. (St. Louis, Mo.) and Molecular Probes, Inc. (Eugene, Oreg.).

TABLE 1

Labels and Labeling Methods

| Label | Source | Linkage Formed |
|---|---|---|
| Amine Labeling | | |
| 2,4,6-trinitrobenzenesulfonic acid | Aldrich | Aryl amine |
| Lissamine ™ rhodamine B sulfonyl chloride | Molecular Probes | Sulfonamide |
| 2',7'-dichlorofluoroscein-5-isothiocyanate | Molecular Probes | Thiourea |
| 4,4-difluoro-5,7-dimethyl-4-bora-3a,4a-diaza-s-indacene-3-propionic acid, sulfosuccinimidyl ester | Molecular Probes | Amide |
| Nahthalene-2,3-dicarboxylaldehyde | Molecular Probes | Isoindole |
| Carboxyl Labeling | | |
| 5-(bromomethyl)fluorescein | Molecular Probes | Ester |
| N-cyclohexyl-N'-(4-(dimethylamino)naphthyl)carbodiimide | Molecular Probes | N-Acylurea |
| 1-ethyl-3-(3-dimethylaminopropyl)-carbodiimide hydrochloride with N-hydroxysuccinimide and 5-aminofluorescein | Pierce Aldrich Molecular Probes | Amide |

In some instances, the proteins separated by the methods of the invention are subjected to further analysis by mass spectroscopy. In such instances, particular labels can be utilized to enhance separation of mass fragments into certain parts of the mass spectrum. Suitable labels in such methods are set forth more fully in application Ser. No. 09/513,395, now U.S. Pat. No. 6,379,971. This application is incorporated herein by reference in its entirety.

Quantitation of detected signals can be performed according to established methods. Peak height and peak area are typically used to quantify the amount of each resolved protein in the final electrophoretic dimension. In some methods, the peak height, peak width at the half height, peak area, and elution time for each peak are recorded. Peak shape (determined as the height to width ratio) can be used as a measure of the quality of the separation method. The resolution potential of the method can be determined by correlating the MW of the protein with the elution time (see, e.g., [30] and [11]). By dividing the overall run time by the average peak width of each protein an estimate of the total number of proteins that can be resolved by the method (e.g., proteins separated by at least one peak width can be considered a "resolved" protein) can be obtained. The reproducibility of the MW estimate can be determined by two methods. In one method, the apparent MW determined for each protein in three replicate runs by establishing the standard curve from one run and using that curve to determine the MW based on elution time from each subsequent run are compared (see, e.g., [21]). In the second approach, the overall error of the method is determined from the standard deviation in the slope of the standard curve created using the data from all three replicate runs.

The labeling and direct detection approaches that can be used with certain methods of the invention can yield improved reproducibility in the quantification of relative protein expression levels compared to the staining and imaging methods utilized in conventional 2-D gels. Staining techniques frequently yield poorly quantitative results because varying amounts of stain are incorporated into each protein and the stained protein must be detected and resolved against the stained background of the gel or electroblotting substrate. Moreover, since the methods utilize combinations of electrophoretic methods, an electropherogram that is directly comparable to archived 2-D gel image data is still obtained. This means that the methods remain comparable to 2-D gel information as compared to other non-electrophoretic based separations (e.g., LC/MS/MS).

F. Exemplary Systems

The methods of the invention are amenable to a variety of different electrophoretic methods. The controlled elution techniques whereby defined fractions are separated spatially, physically or by time, and the labeling and detection methods can be utilized in a number of different electrophoretic techniques. As noted above, the number of electrophoretic methods linked in series is at least two, but can include multiple additional electrophoretic methods as well. In some instances, each electrophoretic method in the series is different; whereas, in other instances certain electrophoretic methods are repeated at different pH or separation matrix conditions.

Despite the general applicability of the methods, as noted above CIEF, CZE and CGE methods are specific examples of the type of electrophoretic methods that can be utilized according to the methods of the invention. In certain methods, only two methods are performed. Examples of such methods include a method in which CIEF is performed first followed by CGE. Labeling is typically performed after CIEF with detection subsequent to elution of protein from the CGE capillary. Protein eluting from the CIEF capillary can be detected using a UV/VIS spectrometer at 214 or 280 nm, for example. In another system, the first method is CZE and the final method is CGE. With this arrangement, labeling is typically performed prior to CZE to enhance resolution as described supra. Detection generally is not performed until the completion of the final electrophoretic separation. A third useful approach involves initially conducting CIEF followed by CZE and CGE. Labeling for such a system is typically done after CIEF and before CZE. Labeling at this point in the overall method avoids alteration of CIEF patterns (see supra) and allows for greater resolution during CZE. Detection is generally conducted at the conclusion of CGE (i.e., with resolved protein within the capillary or after the proteins have eluted from the capillary). These are specific examples of systems that can be utilized; it should be understood that the invention is not limited to these particular systems. Other configurations and systems can be developed using the techniques and approaches described herein.

IV. Samples

The methods of the invention can be used with a wide range of sample types. Essentially any protein-containing sample can be utilized with the methods described herein. The samples can contain a relatively small number of proteins or can contain a large number of proteins, such as all the proteins expressed within a cell or tissue sample, for example.

Samples can be obtained from any organism or can be mixtures of synthetically prepared proteins or combinations thereof. Thus, suitable samples can be obtained, for example, from microorganisms (e.g., viruses, bacteria and fungi), animals (e.g., cows, pigs, horses, sheep, dogs and cats), hominoids (e.g., humans, chimpanzees, and monkeys) and plants. The term "subject" as used to define the source of a sample includes all of the foregoing sources, for example. The term "patient" refers to both human and veterinary subjects. The samples can come from tissues or tissue homogenates or fluids of an organism and cells or cell cultures. Thus, for example, samples can be obtained from whole blood, serum, semen, saliva, tears, urine, fecal material, sweat, buccal, skin, spinal fluid, tissue biopsy or necropsy and hair. Samples can also be derived from ex vivo cell cultures, including the growth medium, recombinant cells and cell components. In comparative studies to identify potential drug or drug targets (see infra), one sample can be obtained from diseased cells and another sample from non-diseased cells, for example.

Sample preparation for the different electrophoretic techniques is set forth above. If the sample contains cellular debris or other non-protein material that might interfere with separation during electrophoresis, such materials can be removed using any of a variety of known separation techniques including, for example, forcibly exuding the sample through sieve material, filtration and centrifugation. Samples whose ionic strength is particularly high can be desalted using established techniques such as dialysis and dilution and reconcentration.

In some instances in which the sample contains salts or other interfering components, buffer exchange can be performed to improve IPE "stacking" and improve reproducibility in elution times and peak shapes for electrophoretic methods. One useful way to implement dialysis to remove interfering compounds is to collect fractions directly in the dialysis chamber of a spin dialysis tube (Gilson/Amicon). The sample can then be spin dialyzed and resuspended in a 10-fold dilution of the running buffer to be utilized in the next electrophoretic separation of the series. This procedure has the advantages that: (1) in the case of CIEF, larger volumes of buffers can be used during electroelution of each fraction without diluting the proteins in each fraction, (2) the same sample volume can be used for each fraction injected into the second dimension and (3) smaller more concentrated sample volumes can be used in the second dimension because the dialyzed proteins can be resuspended in almost any buffer volume after dialysis.

V. Variations

A. Further Analysis

The methods of the invention need not end with the last electrophoretic method of the series. As illustrated in FIG. 1, resolved proteins can be further analyzed by non-electrophoretic methods. Examples of such methods include infra-red spectroscopy,. nuclear magnetic resonance spectroscopy, UV/VIS spectroscopy and complete or partial sequencing. Coupling the current electrophoretic-based method to various mass spectroscopy (MS) methods is one specific example of further analysis that can be conducted. A variety of mass spectral techniques can be utilized including several MS/MS methods and Electrospray-Time of Flight MS methods (see, e.g., [61], [62], [63], and [64]). Such methods can be used to determine at least a partial sequence for proteins resolved by the electrophoretic methods such as a protein sequence tag (for a discussion or protein sequence tags, see, e.g., [65] and [66]). Further discussion regarding combining the electrophoretic separations described herein with mass spectral analysis is set forth in U.S. provisional application No. 60/130,238 entitled "Rapid and Quantitative Protein Expression and Sequence Determination," filed Apr. 20, 1999, and to which this application claims benefit and which is incorporated by reference in its entirety. Other mass spectral methods that can be combined with the methods of the present invention are described in U.S. application Ser. No. 09/513,395, now U.S. Pat. No. 6,379,971, and copending U.S. application Ser. No. 09/513,907, both being incorporated by reference in their entirety.

B. Microfluidic Systems

1. Examples of Configurations

In another variation, the capillaries are part of or formed within a substrate to form a part of a microfluidic device that can be used to conduct the analyses of the invention on a very small scale and with the need for only minimal quantities of sample. In these methods, physical fractions of samples typically are not collected. Instead, resolved proteins are separated spatially or by time. Methods for fabricating and moving samples within microfluidic channels or capillaries and a variety of different designs have been discussed including, for example, U.S. Pat. Nos. 5,858,188; 5,935,401; 6,007,690; 5,876,675; 6,001,231; and 5,976,336, all of which are incorporated by reference in their entirety.

Figure 3A:
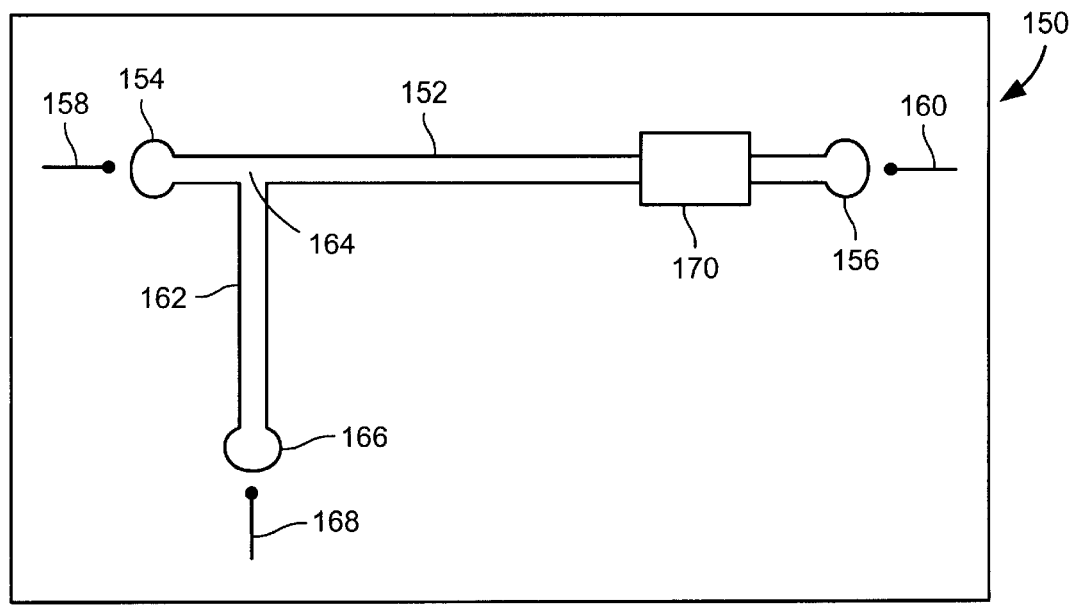
FIGS. 3A and 3B are top-views of certain elements of microfluidic devices that can be utilized to conduct certain electrophoretic methods of the invention.

An example of a general system 150 that can be used with the methods of the present invention is depicted in FIG. 3A. The capillaries or channels are typically formed or etched into a planar support or substrate. A separation capillary 152 extends from an anode reservoir 154 containing anolyte to a cathode reservoir 156. The anode reservoir 154 and the cathode reservoir 156 are in electrical contact with an anode and cathode 158, 160, respectively. A sample injection channel 162 runs generally perpendicular to the separation capillary 152 and one end intersects at an injection site 164 slightly downstream of the anode reservoir 154. The other end of the sample injection capillary 162 terminates at a sample reservoir 166, which is in electrical communication with a sample reservoir electrode 168. A detector 170 is positioned to be in fluid communication with electrophoretic medium passing through the separation capillary 152 and is positioned downstream of the sample injection site 164 and typically somewhat upstream of the cathode reservoir 156. In this particular configuration, fractions are withdrawn into the cathode reservoir 156. Movement of electrophoretic medium through the various channels is controlled by selectively applying a field via one or more of the electrodes 158, 160 168. Application of a field to the electrodes controls the magnitude of the EOF within the various capillaries and hence flow through them.

Figure 3B:
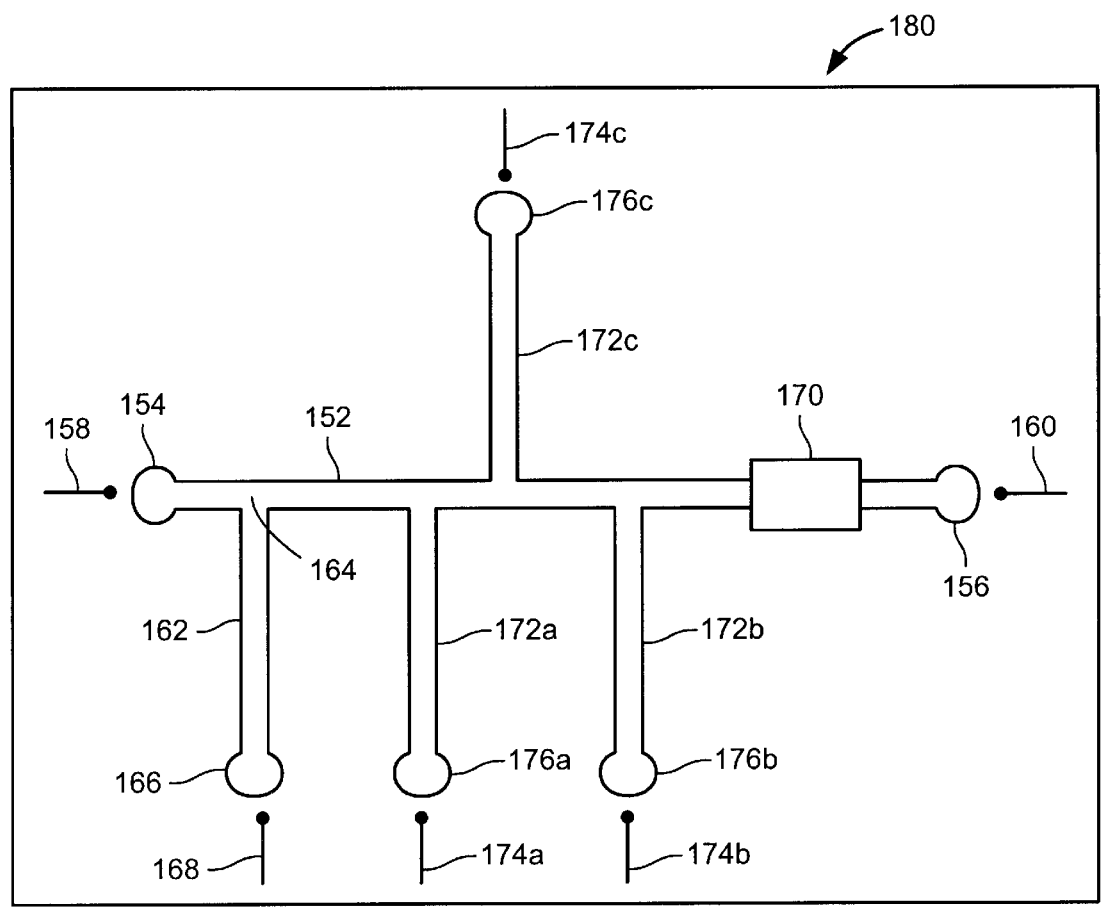

An example of another configuration is illustrated in FIG. 3B. This system 180 includes the elements described in the system shown in FIG. 3A. However, in this arrangement, spacially or temporally resolved fractions can be withdrawn at multiple different locations along the separation capillary 152 via exit capillaries 172a, 172b and 172c. Each of these capillaries includes a buffer reservoir 176a, 176b, 176c, respectively, and is in electrical communication with electrodes 174a, 174b, 174c, respectively. Movement of electrophoretic medium along separation capillary 152 and withdrawal of fractions therefrom into the exit capillaries 172a, 172b and 172c can be controlled by controlling which electrodes along the separation capillary 152 and which of the exit capillary electrodes are activated. Alternatively, or in addition, various microfluidic valves can be positioned at the exit capillaries 172a, 172b and 172c to control flow. Typically, additional detectors are positioned at the various exit capillaries 172a, 172b and 172c to detect protein in fractions withdrawn into these capillaries.

The configuration illustrated in FIG. 3B can be used in a number of different applications. One example of an application for which this type of system is appropriate is a situation in which the type of samples being examined have been well characterized. If for example, certain fractions of proteins of interest have been previously established to fractionate at a particular location in the separation capillary 152, then the exit capillaries 172a, 172b and 172c can be positioned at those locations to allow for selective removal of the protein fraction(s) of interest.

In still another configuration, multiple exit capillaries branch from the end of the separation capillary 152 near the cathode reservoir 156, each exit capillary for withdrawing and transporting separate fractions. In this configuration also, withdrawal of fractionated protein from the separation capillary can be controlled by regulating EOF within the various capillaries and/or by microfluidic valves.

Other components necessary for conducting an electrophoretic analysis can be etched into the support, including for example the reservoirs, detectors and valves discussed supra.

2. Substrates

The substrate upon which the capillary or micro-channel network of the analytical devices of the present invention are formed can be fabricated from a wide variety of materials, including silicon, glass, fused silica, crystalline quartz, fused quartz and various plastics, and the like. Other components of the device (e.g., detectors and microfluidic valves) can be fabricated from the same or different materials, depending on the particular use of the device, economic concerns, solvent compatibility, optical clarity, mechanical strength and other structural concerns. Generally, the substrate is manufactured of a non-conductive material to allow relatively high electric fields to be applied to electrokinetically transport the samples through the various channels.

In the case of polymeric substrates such as plastics, the substrate materials can be rigid, semi-rigid, or non-rigid, opaque, semi-opaque or transparent, depending upon the use for which the material is intended. Plastics which have low surface charge when subjected to the electric fields of the present invention and thus which are of particular utility include, for example, polymethylmethacrylate, polycarbonate, polyethylene terepthalate, polystyrene or styrene copolymers, polydimethylsiloxanes, polyurethane, polyvinylchloride, polysulfone, and the like.

Devices which include an optical or visual detector are generally fabricated, at least in part, from transparent materials to facilitate detection of components within the separation channel by the detector.

2. Channel Structure/Formation

The size and shape of the channels or capillaries formed in the substrate of the present devices can have essentially any shape, including, but not limited to, semi-circular, cylindrical, rectangular and trapezoidal. The depth of the channels can vary, but tends to be approximately 10 to 100 microns, and most typically is about 50 microns. The channels tend to be 20 to 200 microns wide.

Manufacturing of the channels and other elements formed in the surface of the substrate can be carried out by any number of microfabricating techniques that are known in the art. For example, lithographic techniques may be employed in fabricating glass or quartz substrates, for example, using established methods in the semiconductor manufacturing industries. Photolithographic masking, plasma or wet etching and other semiconductor processing technologies can be utilized to create microscale elements in and on substrate surfaces. Alternatively, micromachining methods, such as laser drilling, micromilling and the like, can be utilized. Manufacturing techniques for preparing channels and other elements in plastic have also been established. These techniques include injection molding techniques, stamp molding methods, using for example, rolling stamps to produce large sheets of microscale substrates, or polymer microcasting techniques, wherein the substrate is polymerized within a micromachined mold.

Further guidance regarding other designs and methods for using such microfluidic devices such as described above can be found, for example, in U.S. Pat. Nos. 5,858,188; 5,935,401; 6,007,690; 5,876,675; 6,001,231; and 5,976,336, all of which are incorporated by reference in their entirety.

C. Preliminary Separation by Non-Electrophoretic Technique

The methods can also include an initial separation by a non-electrophoretic technique prior to commencing the electrophoretic separations. Essentially any type of technique capable of separating proteins can be utilized. Suitable methods include, but are not limited to, fractionation in a sulfate gradient, HPLC, ion exchange chromatography and affinity chromatography.

VI. Exemplary Utilities

The methods and apparatus of the invention can be utilized to detect, characterize and/or identify many proteins (e.g., hundreds or thousands of proteins in some methods) by controlling elution of fractionated proteins and utilizing various labeling and detection techniques. Consequently, the methods have multiple utilities including, but not limited to, various analytical applications (e.g., monitoring certain protein levels as a function of external stimuli, or detecting specific proteins in complex compositions for identification purposes), clinical applications (e.g., detecting and/or monitoring compositions of normal and diseased cells and tissues, diagnosing or monitoring disease, testing drug candidates for therapeutic efficacy and toxicity testing) and molecular biology and genetic research (e.g., characterizing or monitoring molecular expression levels of gene products and determining the effects of the addition, mutation, deletion or truncation of a particular gene). In general, the methods and apparatus have utility in proteome research.

More specifically, the invention can be used in the development of protein databases in which, for example, proteins expressed under particular conditions are isolated, quantified, and identified. Using the controlled elution and detection methods described herein, certain methods can be utilized to determine and catalog a variety of chemical and physical characteristics of the resolved proteins, including, but not limited to, pI, and/or apparent molecular weight and/or relative abundance of proteins within a sample. This information can be further cross referenced with a variety of information regarding the source of the sample and the method by which it was collected. Examples of such information include genus, species, age, race, sex, environmental exposure conditions, subject's health, tissue type, method of sample collection and method of sample preparation prior to electrophoresis.

The methods also have value in a variety of comparative studies that can be utilized to identify potential drug targets and/or candidates. For example, the methods can be utilized to identify proteins that are differentially expressed in diseased cells as compared to normal cells. Such differentially expressed proteins can serve as targets for drugs or serve as a potential therapeutic. In a related fashion, the methods can be used in toxicology studies to identify proteins that are differentially expressed in response to particular toxicants. Such differentially expressed proteins can serve as potential targets or as potential antidotes for particular toxic compounds or challenges. The detection and labeling techniques of the invention can facilitate such investigations because these techniques enable even low abundance proteins to be detected and because enhanced reproducibility makes it easier to identify real differences in expression between different samples.

Proteomic studies using certain methods of the invention can detect mutations that result in premature termination of the gene transcript or in amino acid substitutions in the resulting gene product. The methods can also detect post translational modification events associated with disease that are not readily detectable or possible to detect using functional genomics. For example, proteomic methods can detect differences in protein folding, glycosylation patterns, phosphorylation events, and degradation rates.

The results of comparative studies are transferable to a variety of diagnostic applications. For example, the "marker" or "fingerprint" proteins identified during comparative studies as being characteristic of a particular disease can be used to diagnosis individuals to determine if they have the disease correlated with the marker. These markers can also be used in medical screening tests. Once such proteins have been identified, it is not necessary to examine all fractions. Instead, only those fractions potentially containing the marker proteins need be examined. The reproducibility of the methods facilitates such analyses. For systems integrated onto a chip or support (see supra), capillaries can be positioned at the appropriate locations along the separation cavity to withdraw only the relevant fractions potentially containing the marker protein(s) of interest.

As an example of a diagnostic application, proteomic analysis can be utilized in identifying diagnostic markers (e.g., cell surface antigens or serum proteins) for immuno-diagnostic assays. Purified samples of putative diagnostic proteins are recovered during proteomic analysis, and can be used to generate antibodies having specific binding affinity to the proteins. Such antibodies can be used to understand the link between the marker protein and the disease through immunological staining to localize the protein in diseased cells or to rapidly screen patients for the presence of the protein, showing its statistical link to the disease.

The methods of the invention have further utility in conducting structure activity studies. For instance, the methods can be used to determine the effect that certain chemical agents or combination of agents have on protein expression patterns. Alterations to the agent or combination can then be made and protein expression reassessed to determine what effect if any the alteration has on protein expression. Such studies can be useful, for example, in making derivatives of a lead compound identified during initial drug screening trials.

Metabolic engineering studies can also be conducted using the methods of the invention. In such studies, a gene can be genetically engineered to include certain changes or the promoter of a gene be genetically engineered to increase or decrease its relative expression level. The methods described herein can then be used to determine what effect, if any, the genetically engineered changes have on proteins other than the protein encoded by the genetically engineered gene.

The following examples are offered to illustrate, but no to limit the claimed invention.

EXAMPLE 1

CZE Separation of Unlabeled Proteins

Each of five proteins (see Table 2) were obtained from Sigma-Aldrich and were suspended at 5 mg/ml in an aqueous denaturing sample buffer consisting of 25 mM tris (hydroxymethyl)aminomethane phosphate (pH 4.0), 0.5% by weight IGEPAL CA-630 (obtained from Sigma-Aldrich, Cat # I3021), and 1% by weight tris(2-carboxyethylphosphine)hydrochloride (TCEP, obtained from Pierce, Cat # 20490ZZ). The protein samples were denatured in this sample buffer by heating at 95° C. for 15 min. Each of the five denatured protein samples were diluted into a CZE sample buffer to create a final solution consisting of 25 mM tris(hydroxymethyl)aminomethane phosphate buffer (pH 4.0), 8 M Urea, and a final concentration of 0.2 mg/ml of each of the five proteins. Control samples were also prepared of each denatured protein separately at 0.5 mg/ml final concentration in the same sample buffer.

TABLE 2

| Protein Standards | | | |
|---|---|---|---|
| Protein | Cat # | pI | MW (kDa) |
| Hen egg white conalbumin | C 0755 | 6.0, 6.3, 6.6 | 76.0 |
| Bovine serum albumin | B 4287 | 5.4, 5.5, 5.6 | 66.2 |
| Carbonic anhydrase II | T 6522 | 4.5 | 21.5 |
| Rabbit muscle GAPDH | G 2267 | 8.3, 8.5 | 36.0 |
| Bovine ribonuclease A | R 5503 | 9.6 | 13.7 |

The mixed protein sample and each of the control samples were run by CZE in a 60 cm×75 µm fused silica capillary (Beckman Coulter). An 800 µm detection window was located 50 cm from the anodic end of the capillary. A 160 nl sample volume was pressure injected at the anodic end and the separations conducted at 500 V/cm in a 25 mM TRIS-phosphate and 8 M urea running buffer at pH 4.0. Protein detection was accomplished by UV adsorption at 214 nm.

Figure 4:
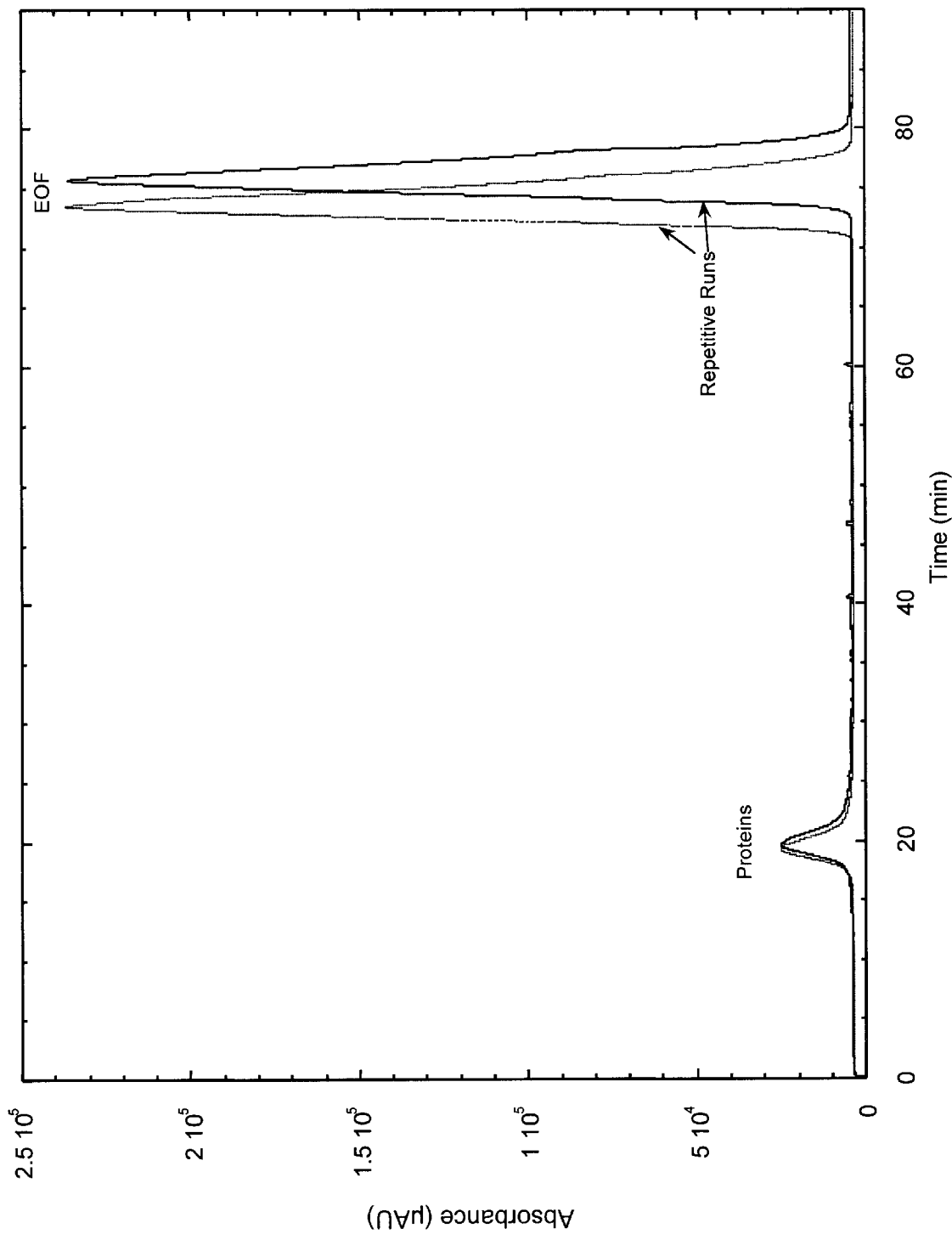
FIG. 4 is an electropherogram for a sample containing five unlabeled proteins (hen egg white conalbumin, bovine serum albumin, bovine carbonic anhydrase II, carbonic anhydrase II, rabbit muscle GAPDH, and bovine ribonuclease A) as obtained following electrophoresis by capillary zone electrophoresis. Absorbance was monitored at 214 nm. Under the conditions of this particular experiment (see Example 1) in which the proteins were unlabeled, the proteins were not resolved.
Figure 5:
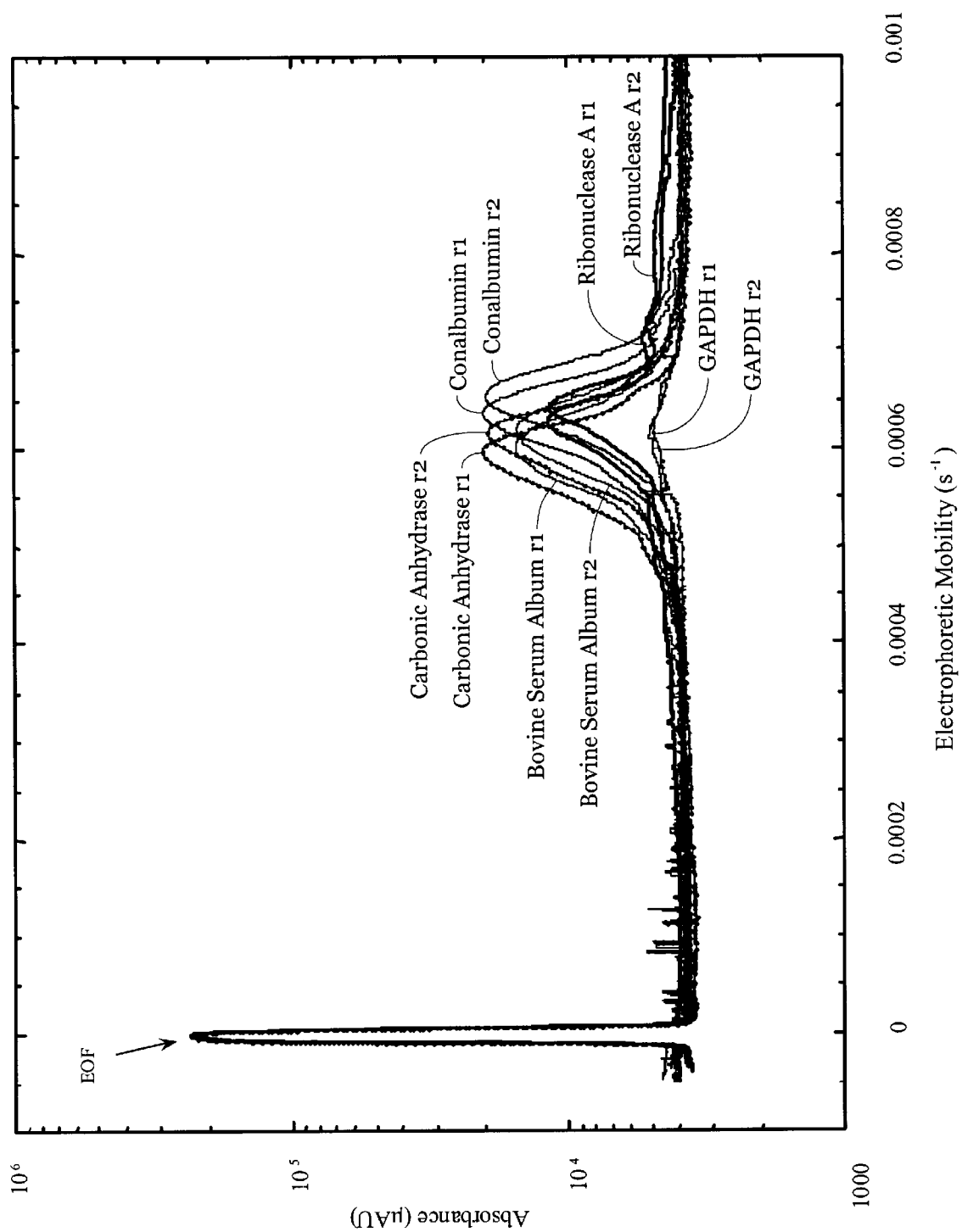
FIG. 5 is a plot of electrophoretic mobility for each of the five proteins listed in FIG. 4 under the same electrophoresis conditions as described in FIG. 4.
Figure 6:
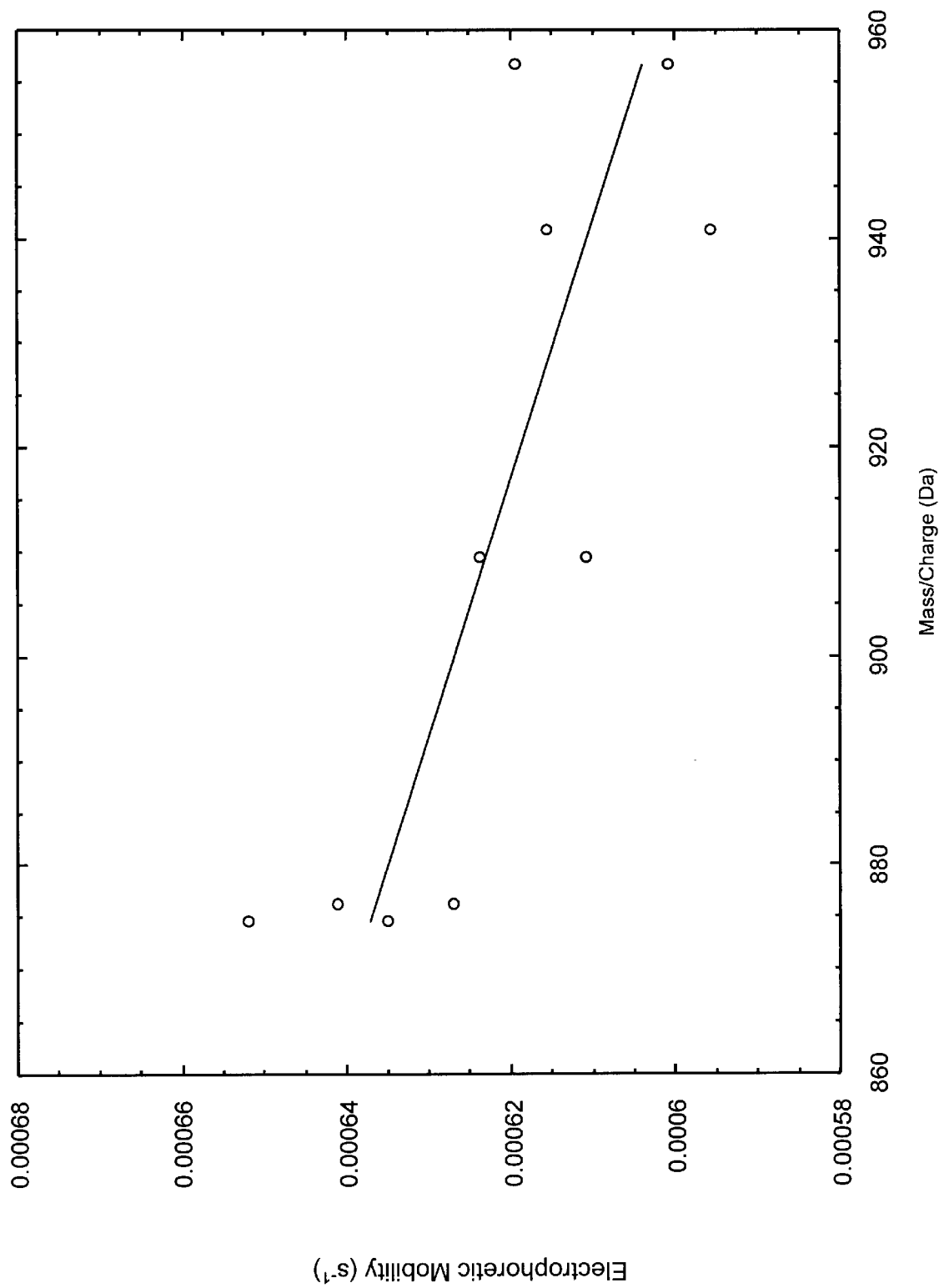
FIG. 6 is a plot showing the correlations between electrophoretic mobility and the predicted mass-to-charge ratio of the proteins at pH 4.0.

The individual unlabeled proteins were not resolved under these conditions (see FIG. 4). The electrophoretic mobility of each protein was determined from replicate runs of the individual protein controls (FIG. 5) and correlated with the predicted mass to charge ratio of the proteins at pH 4.0 (FIG. 6). The mass to charge ratio for each of the unlabeled proteins was determined from the published protein sequences obtained through Genbank in the manner described by Canter, C. R. and Schimmel, P. R., *Biophysical Chemistry*, W. H. Freeman and Co., New York, (1980), which is incorporated by reference in its entirety.

EXAMPLE 2

CZE Separation of Labeled Proteins, with Fraction Collection

Each of the five proteins described in Example 1 was suspended at 10 mg/ml in a denaturing buffer containing 1% by weight of sodium dodecyl sulfate and 1% by volume 2-mercaptoethanol. The proteins were denatured in this buffer by heating at 95° C. for 15 min. The denatured protein samples were labeled with 4-sulfophenylisothiocyanate (SPITC) obtained from Sigma-Aldrich (Cat # 85,782-3) and used as supplied. Labeling was accomplished by adding 0.01 ml of triethylamine, 0.01 ml of 2 M acetic acid and 0.02 ml of a 10% by weight solution of SPITC in water to 0. I ml of each denatured protein sample. The reaction mixture was heated at 50° C. for 24 h.

Figure 7:
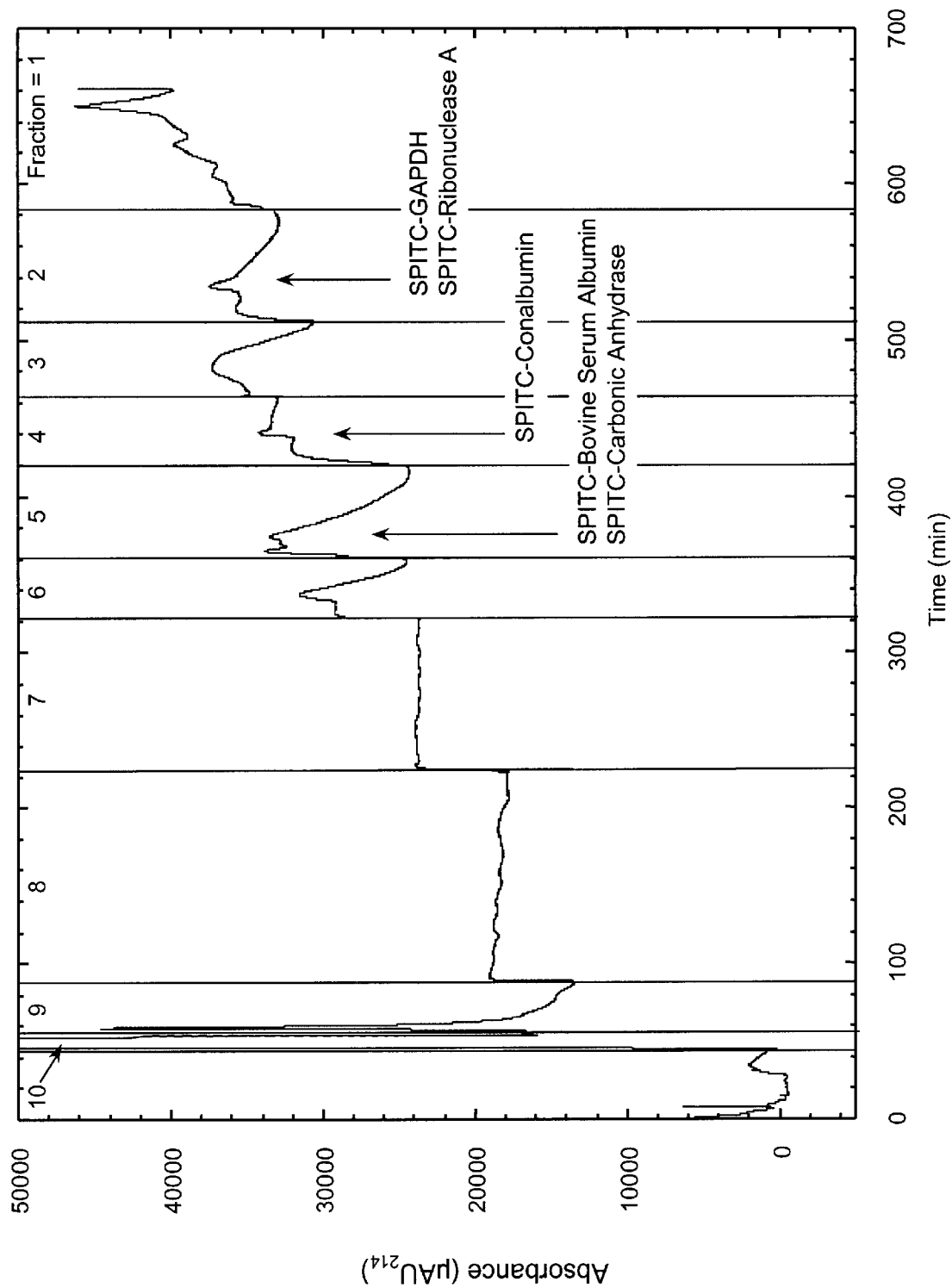
FIG. 7 is an electropherogram obtained during separation of a sample containing five sulfophenylisothiocyanate-labeled proteins (hen egg white conalbumin, bovine serum albumin, bovine carbonic anhydrase II, carbonic anhydrase II, rabbit muscle GAPDH, and bovine ribonuclease A) as obtained following electrophoresis by capillary zone electrophoresis. Absorbance was monitored at 214 nm. Under the conditions of this particular experiment (see Example 2) in which the proteins were labeled, the labeled proteins were partially resolved.

A quantity of 0.05 ml of each of the SPITC-labeled protein standards was mixed together and separated by cZE as described in Example 1, with the exception that the pH of the separation buffer was adjusted to 3.0. The individual SPITC-labeled proteins were resolved (FIG. 7). Thus, this example taken in view of the results for Example 1 in which unlabeled proteins were poorly resolved demonstrates the positive effect that labeling can have when done prior to a CZE separation. Fractions were collected by electroelution into separate vials containing the separation buffer at the times indicated. The identities of the SPITC-labeled proteins were determined by subsequent CGE analysis of the fractions.

EXAMPLE 3

CIEF First Dimension Separation with Fraction Collection

Bovine Serum Albumin, Carbonic Anhydrase, and Conalbumin were used as supplied from Sigma-Aldrich (Table 2). Each protein was denatured as described in Example 1. A 0.01 ml aliquot of each denatured protein sample was added to 0.2 ml of the CIEF focusing buffer. The CIEF focusing buffer consisted of 0.4% by weight hydroxymethyl cellulose solution (Beckman-Coulter eCAP-CIEF Gel Buffer, Cat # 477497) containing 1% by volume pH 3–10 Ampholytes (Fluka, Cat # 10043) and 1% by weight 3-[(3-cholamidopropyl) dimethylammonio]-1-propane sulfonate.

A poly(ethylene glycol)-coated 60 cm long 0.1 mm internal diameter fused silica capillary (Supelcowax 10, Supelco, Cat # 25025-U) was filled with the protein sample in the focusing buffer. The capillary contents were focused between 10 mM phosphoric acid and 20 mM NaOH reservoirs for 7.5 min at 500 V/cm and 25 C. A 0.5 psi pressure gradient was then applied between the anolyte and catholyte reservoirs to facilitate the elution of the focused proteins in the direction of the electroosmotic flow.

Figure 8:
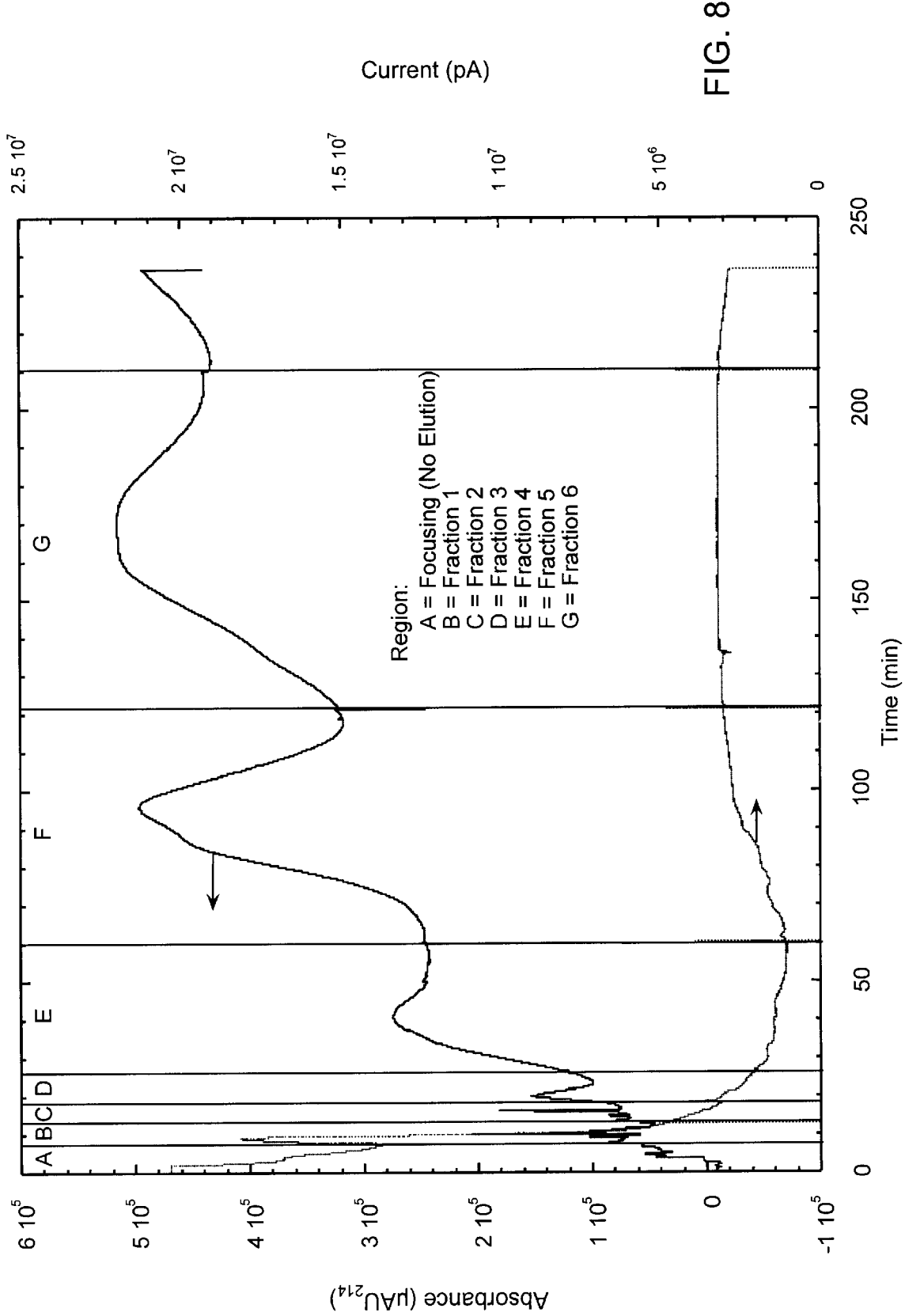
FIG. 8 is an electropherogram obtained during separation of a sample containing the proteins hen white conalbumin, bovine serum albumin, and bovine carbonic anhydrase II, by CIEF.

The protein peaks were detected by monitoring the ultraviolet absorption at 214 nm through an optical window in the capillary positioned 50 cm from the low pH end. The current through the capillary was also monitored (FIG. 8). Fractions (B-G) were collected into 0.05 ml of 20 mM NaOH contained in separate reservoir vials for the times depicted (FIG. 8). Only fractions F and G were found to contain protein (see Example 4). Fraction G was found to contain carbonic anhydrase and no conalbumin or bovine serum albumin. Conalbumin and bovine serum albumin were found to coelute in the peak observed in fraction F. This experiment illustrates the partial separation of a mixture of proteins in a single dimension. Further resolution was achieved in the second dimension (see Example 4).

EXAMPLE 4

CGE Second Dimension Separation of CIEF Fractions

Each of the CIEF fractions (B-G) collected during the CIEF separation described in Example 3 were evaporated in a Savant Model SC210A Spin-Vap to a final volume of 0.005 ml to concentrate any protein present in the fraction. A quantity 0.01 ml of SDS sample buffer was added to each protein concentrate. The SDS sample buffer consisted of 0.1 ml of eCAP SDS sample buffer (Beckman Coulter, Cat # 241525), 0.01 ml of eCAP Orange G Reference Marker (Beckman Coulter, Cat # 241524), and 0.09 ml of anhydrous glycerol.

Each sample was then run in CGE mode using a linear poly(acrylamide)-coated fused silica capillary 60 cm long with a 100 $\mu$m internal diameter. The eCAP SDS 14–200 Gel buffer (Beckman-Coulter Cat # 477416) was used for the separation and in both reservoirs. The separation was conducted at 20° C. and 500 V/cm for 50 min. Ultraviolet detection of the proteins was accomplished at 214 nm through an optical window positioned 50 cm from the sample injection end of the capillary. Molecular weight calibration was conducted in a separate run using eCAP MW Standards (Beckman-Coulter Cat # 477418) as described by the manufacturer. A 100 sec sample injection at 0.5 psi was used to load each sample into the capillary.

Figure 9:
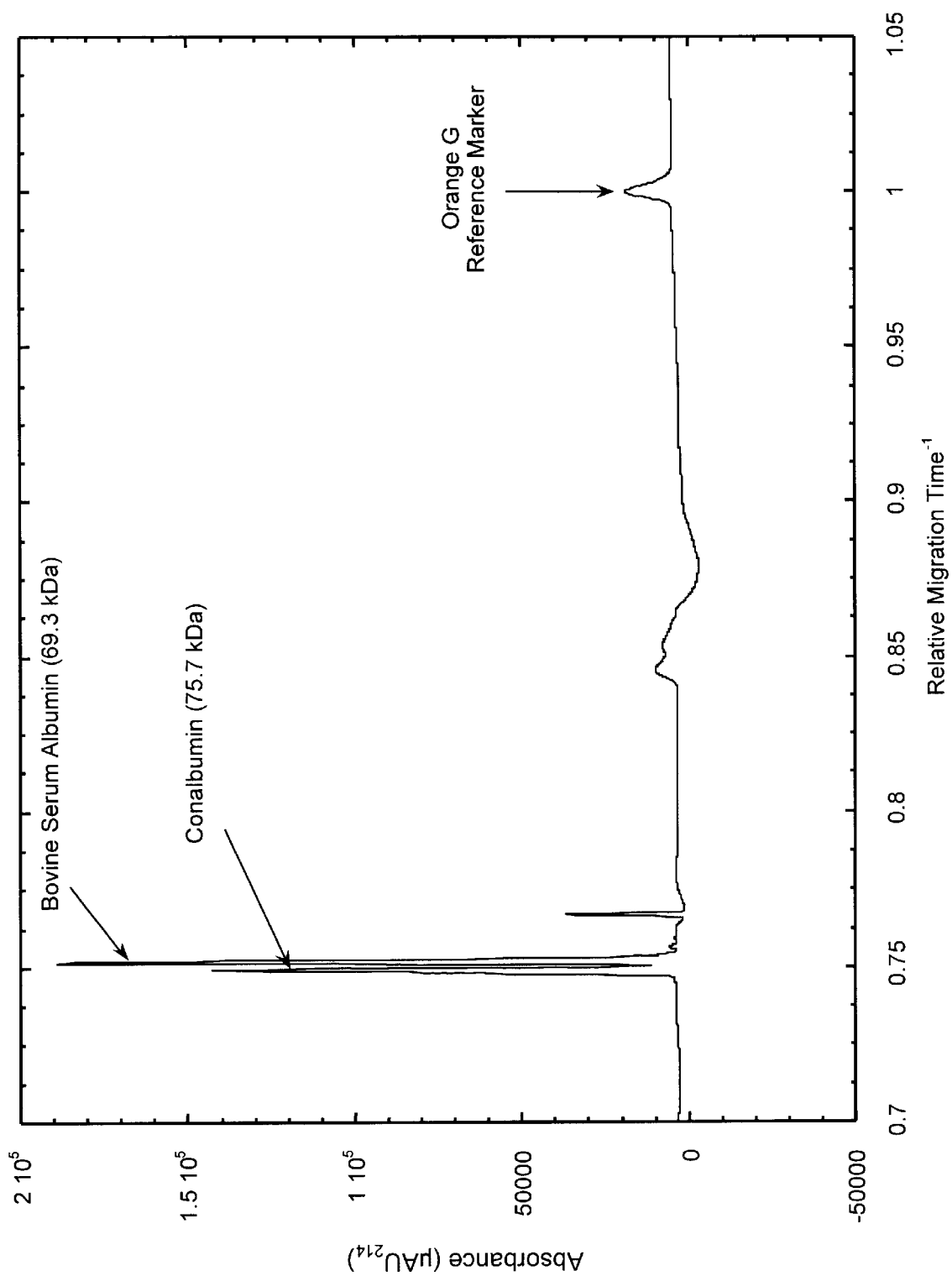
FIG. 9 is an electropherogram of a fraction (fraction F) obtained from the separation by CIEF shown in FIG. 7.
Figure 10:
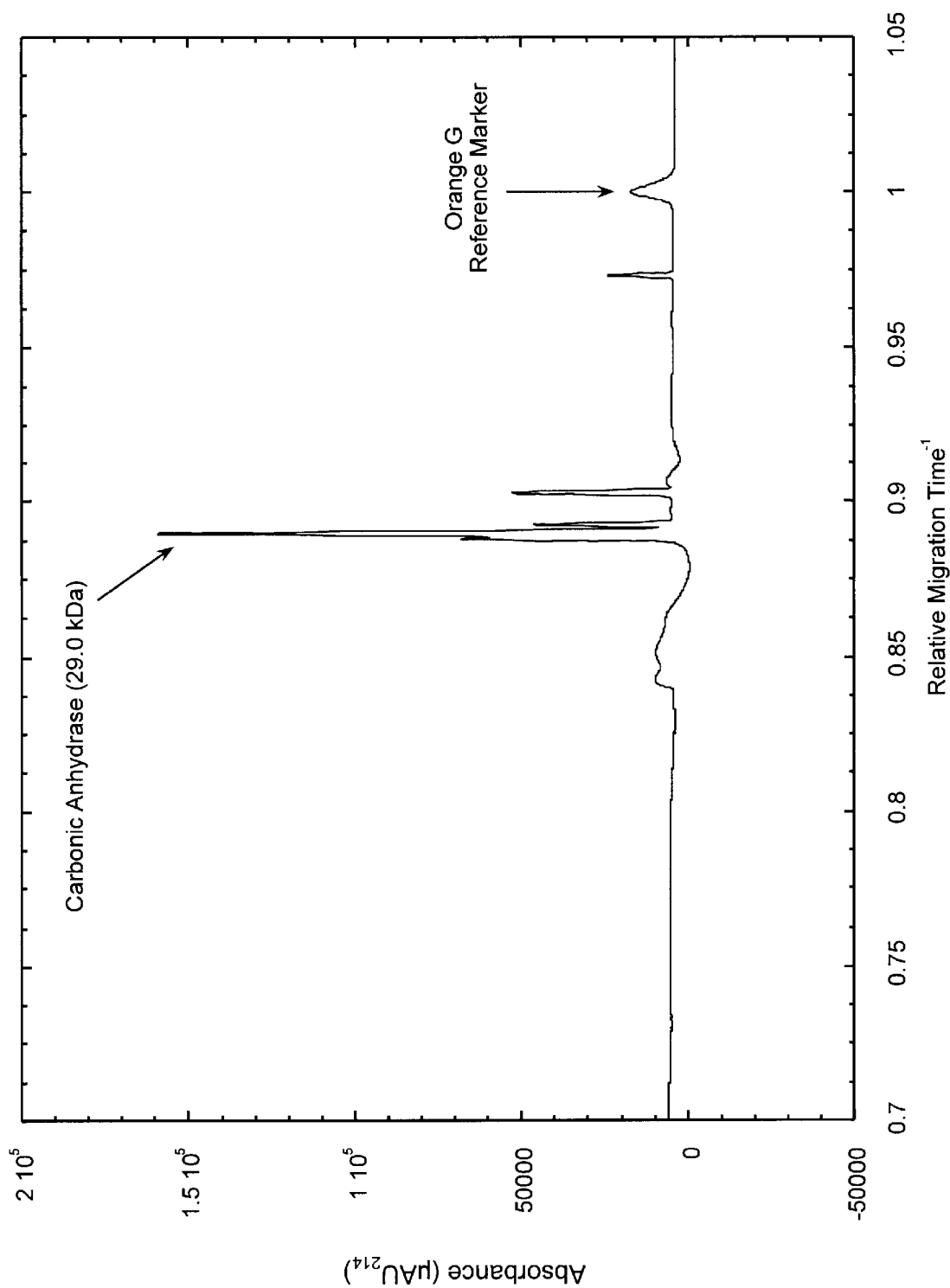
FIG. 10 is an electropherogram of a fraction (fraction G) obtained from the separation by CIEF shown in FIG. 7.

The resulting electropherograms showed no detectable protein in any cIEF fraction except fractions F (FIG. 9) and G (FIG. 10). The molecular weight of the two proteins seen in fraction F (FIG. 9) correspond to that of bovine serum albumin and conalbumin (Table 2). The molecular weight of the protein seen in fraction G (FIG. 10) corresponded to that of carbonic anhydrase (Table 1). It is observed that the second cGE dimension was necessary to fully resolve bovine serum albumin from conalbumin, which were not resolved by a single cIEF mode (Example 3).

EXAMPLE 5

Use of Methods in Proteomics Analysis for Distinguishing Between Healthy and Cancerous Tissue This example illustrates the use of the present invention for distinguishing between healthy and cancerous tissue. The present invention can be used to directly analyze the protein expression pattern of healthy and cancerous and metastasized tissues to elucidate patterns of gene expression and translate such relations to the various aspects of onset, staging and metastases in cancers, such as prostrate, breast, colon and skin.

The methods of the invention can significantly decrease the time necessary to conduct functional genomics analysis of the mechanism of disease and can lead to the identification of new therapeutic targets, diagnostic markers, and drug products (i.e., where a specific cellular protein may itself act as a therapeutic agent). By using proteomic analysis the number of genes that must be investigated is reduced 10-fold (from the 50,000 to 150,000 human genes to the 2,000–10,000 genes actually being expressed to form proteins in the target tissue). Through quantitative comparison of the protein expression pattern of healthy and diseased tissue, the number of candidate genes that may play roles in the progression of the disease is further reduced about 100-fold. Finally, through the subsequent generation of protein sequence tags (PTSs; i.e., a partial amino acid sequence) each of the proteins that show differential expression can be uniquely identified in a manner that allows them to be tracked back to the genome for complete sequencing (e.g., mutation detection).

Initially, tissue samples are obtained from diseased subjects and control subjects (e.g., individuals not known to have the particular cancer being studied). The tissue samples from each individual are homogenized according to known methods. Depending upon the sample, the resulting homogenate is filtered or centrifuged to remove cellular debris. Samples are taken from the homogenate and the proteins therein denatured by adjusting the samples to contain urea (6–8 M), detergent (e.g., 1% by weight sodium dodecyl sulfate) and 1% by weight dithiothreitol. Samples are heated at 95° C. for 15 minutes to speed denaturation.

Samples (5 $\mu$l) are then electrophoresed by CIEF on a column (75 micron inside diameter by 60 cm long). Anolyte is initially 10 mM phosphoric acid and the catholyte is initially 20 mM sodium hydroxide. Separations are conducted at 500 V/cm. Fractions of resolved proteins are eluted by increasing the sodium chloride concentration of the catholyte solution from 10 mM to 100 mM in 96 incremental units. Fractions are collected by sequentially inserting the high pH end of the capillary into 200 l of each salt concentration in catholyte solution contained in the wells of a 96 well plate. The separation current is allowed to reequilibrate before the capillary end is moved to the next fraction.

Prior to labeling, fractions are concentrated using a rotary evaporator. Protein in the collected fractions is labeled by reacting the proteins with fluoroscein isothiocyanate as described in Example 2 for sulfophenylisothiocyanate.

Fractions containing the labeled proteins are separately electrophoresed by CZE. The labeled proteins are diluted into a CZE sample buffer to form a final solution consisting of 25 mM tris(hydroxymethyl)aminomethane phosphate buffer (pH 4.0), 8 M urea, and a final concentration of about 1 mg/ml of protein. The mixed protein sample and each of the control samples are run in CZE mode in a 60 cm×75 μm fused silica capillary (Beckman Coulter). An 800 μm window is located 50 cm from the anodic end of the capillary. A 160 nl sample volume is pressure injected at the anodic end and the separations conducted at 500 V/cm in a 25 mM TRIS-phosphate and 8 M urea running buffer at pH 4.0. Proteins are eluted by the residual EOF in the capillary. Fractions are again collected on the basis of elution time in the wells of a 96 well microtiter plate as the capillary is progressively advanced from one well to the next. Each well contains 200 μl of the cZE separation buffer. This process is repeated with samples from the other fractions collected during CIEF.

Samples from CZE fractions are further resolved by CGE. Fractions from CZE are separately concentrated by rotary evaporation to a final liquid volume of about 5 μl. The protein sample is isolated from crystallized urea by refrigerated (4° C.) centrifugation. Ten microliters of SDS sample buffer is added to each vial of protein concentrate. The SDS sample buffer consists of 100 μl of eCAP SDS sample buffer (Beckman Coulter, Cat # 241525), 10 μl of eCAP Orange G Reference Marker (Beckman Coulter, Cat # 241524), and 90 μl of anhydrous glycerol.

Each sample is run in cGE mode using a linear poly (acrylamide)-coated fused silica capillary 60 cm long with a 100 μm internal diameter. Commercially available eCAP SDS 14-200 Gel buffer (Beckman-Coulter Cat # 477416) is used for the separation and included in both reservoirs. The separation is conducted at 20° C. and 500 V/cm for 50 min. Molecular weight calibration is conducted in a separate run using eCAP MW Standards (Beckman-Coulter Cat # 477418) as described by the manufacturer. A 100 sec sample injection at 0.5 psi is used to load each sample into the capillary. Resolved proteins are detected by fluoroscein fluorescence with a 466 nm laser induced fluorescence detector.

The foregoing process is repeated with multiple samples from diseased and control subjects, as well as replicate runs with samples from the same subjects. The results are then examined to identify proteins whose relative abundance varies between diseased and control subjects. Such proteins are potential markers for the particular disease and/or a drug target or potential drug.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

REFERENCES

1. Kilár, F., "Isoelectric focusing in capillaries," in: CRC Handbook of Capillary Electrophoresis: A Practical Approach, Chp. 4, pgs. 95–109 (CRC Press, Boca Raton, Fla., 1994).
2. Palmieri, R. and J. A. Nolan, "Protein capillary electrophoresis: Theoretical and experimental considerations for methods development," in: CRC Handbook of Capillary Electrophoresis: A Practical Approach, Chp. 13, pgs. 325–368 (CRC Press, Boca Raton, 1994).
3. Wanders, B. J. and F. M. Everaerts, "Isotachophoresis in capillary electrophoresis," in: CRC Handbook of Capillary Electrophoresis: A Practical Approach, Chp. 5, pgs. 111–127 (CRC Press, Boca Raton, Fla., 1994).
4. Anderson, L. and J. Seilharner, "A Comparison of Selected mRNA and Protein Abundances in Human Liver," Electrophoresis, 18:533 (1997).
5. Hochstrasser, D. F., et al., Anal Biochem., 173:424 (1988).
6. O'Farrell, P. H., J Biol. Chem., 250:4007 (1975).
7. Anderson, N. G. and N. L. Anderson, "Twenty years of two-dimensional electrophoresis: Past, present and future," Electrophoresis, 17:443 (1996).
8. Lopez, M. F., "2D Electrophoresis of Target Protein Groups and the Initiation of a Neurological Disease Database," paper presented at the IBC Proteomics conference, Coronado, Calif. (Jun. 11–12, 1998).
9. Gottlieb, M. and M. Chavko, Anal. Biochem., 165:33 (1987).
10. Bio-Rad, "Detection of Proteins in SDS-PAGE: A comparison of gel staining methods," EG Bulletin 1820, Rev B (Bio-Rad Laboratories, Hercules, Calif., 1996).
11. Schneider, L., "Metabolic uncoupling in Escherichia coli during phosphate limited growth," PhD Thesis, Department of Chemical Engineering, (Princeton University, Princeton, N.J., 1997).
12. Merril, C. R., Methods in Enzymology, 182:477 (1990).
13. Wilson, C. M., Methods in Enzymology, 91:236 (1983).
14. Lee, C., A. Levin and D. Branton, Anal. Biochem., 166:308 (1987).
15. Dzandu, J. K., J. F. Johnson and G. E. Wise, Anal. Biochem., 174:157 (1988).
16. Steinberg, Jones, Haugland and Singer, Anal. Biochem., 239:223 (1996).
17. Merril, C. R., N. Arold, D. Taube and W. Ehrhardt, Electrophoresis, 9:255 (1981).
18. Garfin, D. E., Methods in Enzymology, 182:425 (1990).
19. Laemmli, U. K., Nature, 227:680 (1970).
20. Corthals, G. L., M. P. Molloy, B. R. Herbert, K. L. Williams, and A. A. Gooley, "Prefractionation of protein samples prior to two-dimensional electrophoresis," Electrophoresis, 18:317 (1997).
21. Lopez, M. F., and W. F. Patton, "Reproducibility of polypeptide spot positions in two-dimensional electrophoresis of ribosomal and nuclear proteins," Electrophoresis, 18:338 (1997).
22. McKee, A., "The Yeast Proteome," paper presented at the IBC Proteomics conference, Coronado, Calif. (Jun. 11–12, 1998).
23. Anderson, L., "Pharmaceutical Proteomics: Targets, mechanisms and function," paper presented at the IBC Proteomics conference, Coronado, Calif. (Jun. 11–12, 1998).
24. Parekh, R. B., "Use of Proteomics in pre-clinical pharmaceutical research," paper presented at the IBC Proteomics conference, Coronado, Calif. (Jun. 11–12, 1998).
25. BioRad Molecular Imager FX and PDQuest 2-D analysis software seminar, presented at the IBC Proteomics conference, Coronado, Calif. (Jun. 11–12, 1998).
26. Patton, W. F., "Defining protein targets for drug discovery using Proteomics," paper presented at the IBC Proteomics conference, Coronado, Calif. (Jun. 11–12, 1998).
27. Ramsby, M., G. Makowski, and E. Khairallah, "Differential detergent fractionation of isolated hepatocytes:

27. ... Biochemical, immunochemical, and two-dimensional gel electrophoresis characterization of cytoskeletal and non-cytoskeletal compartments," *Electrophoresis*, 15:265 (1994).
28. Blomber, A., L. Biomberg, J. Norbeck, S. J. Fey, P. Mose-Larsen, M. Larsen, P. Roepstorff, H. Degand, M. Boutry, A. Posch and A. Görg, *Electrophoresis*, 16:1935 (1995).
29. Corbett, J. M., M. J. Dunn, A. Posch and A. Görg, *Electrophoresis*, 15:1205 (1994).
30. Beckman Instruments, "eCAP SDS 200: Fast, reproducible, quantitative protein analysis," BR2511B (Beckman Instruments, Fullerton, Calif., 1993).
31. Anderson, N. L. et al., "An updated two-dimensional gel database of rat liver proteins useful in gene regulation and drug effects studies, *Electrophoresis*, 16:1997 (1995).
32. Franzén, F., S. Linder, A. A. Alaiya, E. Eriksson, K. Fujioka, A. -C. Bergman, H. Jörnvall, G. Auer, "Analysis of polypeptide expression in benign and malignant human breast lesions," *Electrophoresis*, 18:582 (1997).
33. Guttman, A., J. A. Nolan and N. Cooke, "Capillary sodium dodecyl sulfate gel electrophoresis of proteins, *J. Chromatogr.*, 632:171 (1993).
34. Clauser, K. R., "Managing high-throughput data acquisition and analysis in LC/MS/MS-based Proteomics," paper presented at the IBC Proteomics conference, Coronado, Calif. (Jun. 11–12, 1998).
35. P/ACE™ Laser-induced fluorescence Detectors, BR-8118A (Beckman Instruments, Fullerton, Calif., 1995).
36. Wilm, M. and Mann, M., "Analytical properties of the nanoelectrospray ion source," *Anal. Chem.*, 68:1–8 (1996).
37. Steiner, S., "Proteome methods to profile mechanisms of toxicity," paper presented at the IBC Proteomics conference, Coronado, Calif. (Jun. 11–12, 1998).
38. Amott, D., "Protein differential display and mass spectrometry in the study of congestive heart failure," paper presented at the IBC Proteomics conference, Coronado, Calif. (Jun. 11–12, 1998).
39. Witzmann, F. A., C. D. Flutz, and J. F. Wyman, "Two-dimensional electrophoresis of precision-cut testis slices: Toxicologic application," *Electrophoresis*, 18:642 (1997).
40. Hjertén, S., J. -L. Liao and K. Yao, "Theoretical and experimental study of high-performance electrophoretic mobilization of isoelectrically focused protein zones, *J. Chromatogr.*, 387:127 (1987).
41. Kim, K. W., *J. Chromatogr.*, 559:401 (1991).
42. Satow, T. et al., "The effecto of salts on the separation of bioactive peptides by capillary electrophoresis," *J. High Resolut. Chromatogr.*, 14:276 (1991).
43. Shihabi, Z. K. and L. L. Garcia, "Effects of sample matrix on separation by capillary electrophoresis," in: CRC Handbook of Capillary Electrophoresis: A Practical Approach, Chp. 20, pgs. 537–548 (CRC Press, Boca Raton, Fla., 1994).
44. Garfin, D. E., *Methods in Enzymology*, 182:425 (1990).
45. Jorgenson, J. W. and K. D. Lukacs, "Zone electrophoresis in open-tubular glass capillaries: preliminary data on performance," *J. High Resolut. Chromatogr. Commun.*, 4:230 (1981).
46. Jorgenson, J. W., and K. D. Lukacs, "Zone electrophoresis in open tubular capillaries," *Anal. Chem.*, 53:1298 (1981).
47. Mc Cormick, R. M., "Capillary zone electrophoresis of peptides," in: CRC Handbook of Capillary Electrophoresis: A Practical Approach, Chp. 12, pgs. 287–323 (CRC Press, Boca Raton, Fla., 1994).
48. Aebersold, R., "Proteome analysis: Biological assay or data archive?," paper presented at the IBC Proteomics conference, Coronado, Calif. (Jun. 11–12, 1998).
49. Cobb, K. A. and M. Novotny, "High-sensitivity peptide mapping by capillary zone electrophoresis and microcolumn liquid chromatography, using immobilized trypsin for protein digestion, *Anal. Chem.*, 61:2226 (1989).
50. Cantor, C. R. and P. R. Schimmel, Biophysical Chemistry (W. H. Freeman & Co., NY, 1980).
51. Hjertén, S., "Free zone electrophoresis," *Chromatogr. Rev.*, 9:122 (1967).
52. Martinek, K., Goldmacher, V. S., Klibanov, A. M., and Berezin, I. V., "Denaturing agents (urea, acrylamide) protect enzymes against irreverisble thermoinactivation: A study with native and immobilized alpha-chymotrypsin and trypsin," *FEBS Lett.*, 51:152–155 (1975).
53. Altria, K. D. and C. F. Simpson, "Measurement of electroendosmosis in high-voltage capillary electrophoresis," *Anal. Proc.*, 23:453 (1986).
54. Camilleri, P. and G. N. Okafo, "Replacement of H20 by D20 in capillary zone electrophoresis can increase resolution of peptides and proteins," *J. Chem. Soc. Chem. Commun.*, 3:196 (1991).
55. Camilleri, P., G. N. Okafo, C. Southan, and R. Brown, "Analytical and micropreparative capillary electrophoresis of the peptides from calcitonin," *Anal. Biochem.*, 198:36 (1991).
56. Okafo, G. N. and P. Camilleri, "Capillary electrophoretic separation in both H2O and [2H]2O-based electrolytes can provide more information on tryptic digests, *J. Chromatogr.*, 547:551 (1991).
57. Schwer, C. and F. Lottspeich, "Analytical and micropreparative separation of peptides by capillary zone electrophoresis using discontinuous buffer systems," J. Chromatogr., 623:345 (1992).
58. Foret, F., E. Szoko and B. L. Karger, "On-column transient and coupled column isotachophoretic preconcentration of protein samples in capillary zone electrophoresis," *J. Chromatogr.*, 608:3 (1992).
59. Lowry, O., N. Rosebrough, A. Farr and R. Randall, *J. Biol. Chem.*, 193:265–275 (1951).
60. Anderson, N. L., "Pharmaceutical Proteomics: Targets, mechanism, and function," paper presented at the IBC Proteomics conference, Coronado, Calif. (Jun. 11–12, 1998).
61. Meng, C. K., M. Mann and J. B. Fenn, Z. Phy. D: *Atoms, Mol. Clusters*, 10:361–368 (1988).
62. Karas, M. and F. Hillenkamp, *Anal. Chem.* 60:2299 (1988).
63. Hillenkamp, F., M. Jaras, R. C. Beavis and B. T. Chait, *Anal. Chem.* 63:1193A (1991).
64. Beavis, R. C. and B. T. Chait, "Matrix-assisted laser desorption mass spectrometry of proteins," preprint, http://www.proteometrics.com/methods/contents.htm (1994).
65. Clauser, K. R., S. C. Hall, D. M. Smith, J. W. Webb, L. E. Andrews, H. M. Tran, L. B. Epstein, and A. L. Burlingame, *Proc. Natl. Acad. Sci (USA)*, 92:5072–5076 (1995).
66. Li, G., M. Walthan, N. L. Anderson, E. Unworth, A. Treston and J. N. Weinstein, "Rapid mass spectrometric identification of proteins from two-dimensional polyacrylamide gels after in gel proteolytic digestion," *Electrophoresis*, 18:391–402 (1997).
67. Stevens, F. J., "Method of electric field flow fractionation wherein the polarity of the electric field is periodically reversed," U.S. Pat. No. 5,133,844, (Jul. 28, 1992).

68. Gupta N. R., Nadim A., Haj-Hariri H., Borhan A., "Stability of the Shape of a Viscous Drop under Buoyancy-Driven Translation in a Hele-Shaw Cell," *J Colloid Interface Sci*, 222(1):107–116 (2000).
69. Sanger, F., *Biochem. J.*, 39:507 (1945).
70. Creighton, T. E., *Proteins: Structures and Molecular Principles* (W. H. Freeman, NY, 1984).
71. Niederwieser, A., "Thin-layer chromatography of amino acids and derivatives," in: *Methods in Enzymology*, 25:60–99 (1972).
72. Hirs, C. H. W., M. Halmann and J. H. Kycia, "Dinitrophenylation and inactivation of bovine pancreatic ribonuclease A," *Arch. Biochem. Biophys.*, 111:209–222 (1965).
73. Gray, W. R., "End-group analysis using dansyl chloride," in: *Methods in Enzymology*, 25:121–137 (1972).
74. Stark, G. R., "Use of cyanate for determining NH2-terminal residues in protein," in: *Methods in Enzymology*, 25:103–120 (1972).
75. Niall, H. D., "Automated Edman degradation: the protein sequenator," in: *Methods in Enzymology*, 27:942–1011 (1973).
76. Galella, G. and D. B. Smith, "The cross-linking of tubulin with immidoesters," *Can. J. Biochem.*, 60:71–80 (1982).
77. Lomant, A. J. and G. Fairbanks, "Chemical probes of extended biological structures: synthesis and properties of the cleavable protein crosslinking reagent 35S.dithiobis (succinimidyl propionate), *J. Mol. Biol.*, 104:243–261 (1976).
78. Solomons, T. W. G, Organic Chemistry (John Wiley & Sons, NY, 1976).
79. Novotny et al., *Anal. Chem.*, 63:408 (1991).
80. Novotny etal., *J. Chromatography*, 499:579 (1990).
81. Merrifield, B., *Science*, 232:341–347 (1986).
82. Horton, H. R. and D. E. Koshland, Jr., *Methods in Enzymology*, 25:468 (1972).
83.. Yamada, H., Imoto, T., Fujita, K., Okazaki, K. and M. Motomura, "Selective modification of aspartic acid-101 in lysozyme by carbodlimide reaction," *Biochem.*, 20:4836–4842.
84. Grabarek, Z. and J. Gergely, "Zero-length crosslinking procedure with the use of active esters," *Anal. Biochem.* 185:131–135 (1990).

What is claimed is:

1. A method for separating a plurality of proteins in an initial sample, comprising
    (a) performing a plurality of capillary electrophoretic methods in series, each method comprising electrophoresing a sample obtained from the preceding method in the series, except the first method of the series in which the sample is the initial sample, and wherein
        at least one of the plurality of methods is capillary isoelectric focusing electrophoresis (CIEF) or capillary zone electrophoresis (CZE) and the at least one method is conducted under conditions such that electroosmotic flow is less than or equal to $0.5 \times 10^{-6}$ cm$^2$/V-s; and
    (b) detecting resolved proteins from the final electrophoretic method.

2. The method of claim 1, wherein the plurality of capillary electrophoretic methods are selected from the group consisting of capillary isoelectric focusing electrophoresis, capillary zone electrophoresis and capillary gel electrophoresis.

3. The method of claim 1, wherein the plurality of capillary electrophoretic methods are two methods, the first electrophoretic method being capillary isoelectric focusing electrophoresis and the second electrophoretic method being capillary gel electrophoresis.

4. The method of claim 1, wherein the plurality of capillary electrophoretic methods are two methods, the first electrophoretic method being capillary zone electrophoresis and the second electrophoretic method being capillary gel electrophoresis.

5. The method of claim 1, wherein the plurality of capillary electrophoretic methods are three methods, the first, second and third electrophoretic methods being capillary isoelectric focusing electrophoresis, capillary zone electrophoresis and capillary gel electrophoresis, respectively.

6. The method of claim 1, wherein
    the performing further comprises repeating the electrophoresing step multiple times for each electrophoretic method, each time with a different sample containing only a subset of the plurality of resolved proteins from the immediately preceding method in the series, whereby a plurality of resolved proteins for each of the different samples is obtained; and
    the detecting comprises detecting resolved proteins from each of the different samples from the final electrophoretic method.

7. The method of claim 1, wherein the detecting comprises detecting resolved proteins contained in an electrophoretic medium as the electrophoretic medium passes a detector.

8. The method of claim 1, wherein the detecting comprises detecting protein within a separation cavity utilized to perform the final electrophoretic method.

9. The method of claim 1, further comprising quantifying resolved proteins from the final electrophoretic method.

10. The method of claim 7, further comprising quantifying resolved protein from an electrical signal from the detector.

11. The method of claim 1, further comprising analyzing resolved proteins from the final electrophoretic method by a technique other than electrophoresis.

12. The method of claim 11, wherein the analyzing comprises conducting mass spectrometry with the resolved proteins.

13. The method of claim 1, wherein at least one of the plurality of capillary electrophoretic methods utilizes a capillary adapted to reduce electroosmotic flow within the capillary.

14. The method of claim 13, wherein the internal surface of the capillary is coated with an agent effective to reduce electroosmotic flow.

15. The method of claim 14, wherein the agent is selected from the group consisting of polyacrylamide, polyethylene glycol and polyethylene oxide.

16. The method of claim 13, wherein an induced counter current is generated to counteract electroosmotic flow within the capillary.

17. The method of claim 13, wherein the capillary contains a porous plug positioned upstream from where sample is introduced.

18. The method of claim 17, wherein the plug is composed of a polymeric material capable of forming a gel.

19. The method of claim 18, wherein the polymeric material comprises polymerized acrylamide with diacrylamide crosslinkers or agarose.

20. The method of claim 1, wherein one of the plurality of methods is capillary zone electrophoresis, and the electrophoresing is performed with an electrophoretic medium having a pH that reduces electroosmotic flow to a selected level.

21. The method of claim 1, wherein the plurality of electrophoretic methods are capillary electrophoresis methods conducted with microcapillaries fabricated within a substrate.

22. The method of claim 1, wherein one of the plurality of electrophoretic methods is capillary isoelectric focusing electrophoresis, and the electrophoresing is conducted with an electrophoretic medium lacking a polymeric agent.

23. The method of claim 1, wherein one of the plurality of electrophoretic methods is capillary isoelectric focusing electrophoresis, and the electrophoresing is conducted with an electrophoretic medium containing a polymeric agent.

24. The method of claim 1, wherein the electrophoresing step for each method comprises withdrawing the resolved proteins from an end of the capillary towards which proteins migrate during electrophoresing.

25. The method of claim 1, wherein the electrophoresing step for each method comprises withdrawing the resolved proteins from different locations located between the two ends of the capillary.

26. The method of claim 1, wherein the electrophoresing step for at least one of the plurality of capillary electrophoretic methods comprises eluting resolved proteins by electrophoretic mobility, electroosmotic flow or hydrodynamic pressure.

27. The method of claim 1, further comprising analyzing the detected proteins to determine one or more chemical or physical characteristics of the detected proteins.

28. The method of claim 27, wherein the one or more chemical or physical characteristics are selected from the group consisting of molecular weight, complete or partial amino acid sequence, isoelectric point, relative or absolute abundance and combinations of the foregoing.

29. A method for separating a plurality of proteins in an initial sample, comprising
  (a) performing a plurality of capillary electrophoretic methods in series, each method comprising electrophoresing a sample obtained from the preceding method in the series, except the first method of the series in which the sample is the initial sample, whereby a plurality of resolved proteins are obtained;
  (b) detecting resolved proteins from the final electrophoretic method;
  (c) repeating steps (a) and (b) under the same conditions, wherein the initial sample for the first iteration of the method is from a first source and the initial sample for the second iteration of the method is from a second source; and
  (d) comparing the relative abundance of one or more of the resolved proteins obtained from the first source and the second source as detected from the final electrophoretic method.

30. The method of claim 29, wherein the first source is a subject having a disease and the second source is a control subject and wherein proteins identified during the comparing step as having different relative abundances between the two sources are potential markers, targets or therapeutics for the disease.

31. The method of claim 30, wherein the initial sample is obtained from a patient and further comprising determining whether the resolved proteins obtained from the final electrophoretic method include a least one protein marker known to be correlated with a disease, the detection of the protein marker(s) indicating that the patient has the disease or is susceptible to the disease.

32. A method for separating a plurality of proteins, comprising (a) performing a plurality of electrophoretic methods in series, wherein the method or methods preceding the final method comprise withdrawing and collecting multiple fractions containing proteins resolved during the electrophoretic method, and wherein each electrophoretic method is conducted with a sample from a fraction collected in the preceding electrophoretic method, except the first electrophoretic method which is conducted with a sample containing the plurality of proteins and the final electrophoretic method which is conducted with a sample from one or more fractions obtained in the penultimate electrophoretic method;
  (b) labeling the plurality of proteins or labeling protein contained in one or more collected fractions prior to conducting the last electrophoretic method; and
  (c) detecting one or more labeled, resolved proteins obtained following the final electrophoretic method.

33. The method of claim 32, wherein the detecting step comprises detecting protein with a detector in fluid communication with a separation cavity containing an electrophoretic medium utilized during the final electrophoretic method.

34. The method of claim 32, wherein one of the plurality of electrophoretic methods is capillary zone electrophoresis and the labeling step is conducted prior to conducting the capillary zone electrophoresis method.

35. The method of claim 32, wherein one of the plurality of electrophoretic methods is capillary isoelectric focusing and the labeling step is performed subsequent to the capillary isoelectric focusing method.

36. The method of claim 32, wherein one of the plurality of electrophoretic methods is capillary isoelectric focusing and the labeling step is performed prior to the capillary isoelectric focusing method.

37. A method for separating a plurality of proteins, comprising
  (a) performing one or more capillary electrophoretic methods, each of the one or more methods comprising
    (i) electrophoresing a sample containing multiple proteins within an electrophoretic medium contained within a capillary; and
    (ii) withdrawing and collecting multiple fractions containing proteins resolved during the electrophoresing step, and
    wherein each method is conducted with a sample from a fraction collected in the preceding electrophoretic method, except the first electrophoretic method which is conducted with a sample containing the plurality of proteins;
  (b) labeling the plurality of proteins or labeling protein contained in one or more collected fractions prior to conducting the last electrophoretic method; and
  (c) conducting a final capillary electrophoresis method comprising electrophoresing a sample obtained from one or more fractions obtained from the preceding method in a final capillary and detecting resolved protein within, or withdrawn from, the final capillary.

38. The method of claim 37, wherein the one or more capillary electrophoresis methods is capillary isoelectric focusing electrophoresis and the final capillary electrophoresis method is capillary gel electrophoresis.

39. The method of claim 37, wherein the one or more capillary electrophoresis methods is capillary zone electrophoresis and the final capillary electrophoresis method is capillary gel electrophoresis.

40. The method of claim 37, wherein the one or more capillary electrophoresis methods is two methods, the first method being capillary isoelectric focusing and the second method being capillary zone electrophoresis, and the final capillary electrophoresis method is capillary gel electrophoresis.

41. A method for separating a plurality of proteins in an initial sample, comprising:
   (a) performing a plurality of electrophoretic methods in series, each method comprising
      electrophoresing within an electrophoretic medium a sample containing multiple proteins whereby fractions containing a subset of the multiple proteins are isolated physically, temporally or spatially, and
      wherein the sample electrophoresed is obtained from a fraction isolated during the immediately preceding method in the series, except the first method of the series in which the sample is the initial sample; and
   (b) detecting isolated proteins from the final electrophoretic method;
   (c) analyzing the isolated proteins to determine one or more chemical or physical characteristics of each of the isolated proteins; and
   (d) storing the one or more chemical or physical characteristics into a database with information about the initial sample.

42. The method of claim 41, wherein the one or more chemical or physical characteristics are selected from the group consisting of molecular weight, complete or partial amino acid sequence, isoelectric point, relative or absolute abundance and combinations of the foregoing.

43. The method of claim 42, wherein the information about the sample is selected from the group consisting of genus, species, age, race, sex, or health of the subject from which the initial sample was obtained, tissue type from which the sample was obtained, method of collection of the initial sample, and method of preparation of the initial sample prior to electrophoresis.

44. A method for separating a plurality of proteins in an initial sample, comprising:
   (a) performing a preliminary separation of the plurality of proteins by a non-electrophoretic technique to obtain multiple fractions, wherein each fraction contains a subset of the plurality of proteins and the preliminary separation separates at least some of the plurality of proteins according to differences in amino acid sequence;
   (b) performing a plurality of electrophoretic methods in series, each method comprising
      electrophoresing a sample containing multiple proteins, whereby a plurality of resolved proteins are obtained, and
      wherein the sample electrophoresed contains only a subset of the plurality of resolved proteins from the immediately preceding method in the series, except the first electrophoretic method of the series in which the sample is from one of the multiple fractions; and
   (c) detecting resolved proteins from the final electrophoretic method.

45. The method of claim 44, wherein the non-electrophoretic method is selected from the group consisting of separation by sulfate gradient, HPLC, ion exchange chromatography, affinity chromatography.

46. A method for separating a plurality of proteins in an initial sample, comprising
   (a) performing a plurality of capillary electrophoretic methods in series, wherein
      the method or methods preceding the final method comprises withdrawing and collecting multiple fractions containing proteins resolved during the electrophoretic method,
      each electrophoretic method is conducted with a sample from a fraction collected in the preceding electrophoretic method, except the first electrophoretic method which is conducted with a sample containing the plurality of proteins and the final electrophoretic method which is conducted with a sample from one or more fractions obtained in the penultimate electrophoretic method; and
      the plurality of capillary electrophoretic methods include at least one of the methods selected from the group consisting of capillary isoelectric focusing (CIEF), capillary zone electrophoresis (CZE) and capillary gel electrophoresis (CGE);
   (b) labeling the proteins in the initial sample or labeling resolved protein(s) obtained from at least one of the capillary electrophoresis methods prior to conducting the last electrophoretic method, wherein
      if the plurality of methods includes a CIEF method, labeling is performed after the CIEF method;
      if the plurality of methods includes a CZE method, labeling is performed before the CZE method; and
      if the plurality of methods include a CGE method, labeling is performed before the CGE method; and
   (c) detecting labeled proteins from the final electrophoretic method.

47. The method of claim 46, wherein the plurality of methods includes a CIEF method and labeling is performed after the CIEF method.

48. The method of claim 46, wherein the plurality of methods includes a CZE method and labeling is performed before the CZE method.

49. The method of claim 46, wherein the plurality of methods include a CGE method and labeling is performed before the CGE method.

50. The method of claim 46, wherein the label is selected from the group consisting of a radiolabel, a chromophore, a fluorophore, an electron dense agent, an NMR spin label and a tag suitable for detection by mass spectroscopy.

51. The method of claim 50, wherein the label is a fluorophore.

52. The method of claim 50, herein the label is a tag suitable for detection by mass spectroscopy.

53. A method for separating a plurality of proteins in an initial sample, comprising:
   (a) performing a plurality of capillary electrophoretic methods in series, each method comprising electrophoresing a sample obtained from the preceding method in the series, except the first method of the series in which the sample is the initial sample, whereby one or more resolved proteins are obtained, and wherein
      at least one of the methods is a capillary isoelectric focusing method in which electrophoresing is performed in an electrophoretic medium and comprises eluting resolved proteins by electroelution, electroelution comprising (i) altering the salt concentration of the electrophoretic medium, and/or (ii) pH mobilization of resolved proteins; and
   (b) detecting resolved protein from the final electrophoretic method.

54. The method of claim 53, wherein electroelution is accomplished by altering the salt concentration of the electrophoretic medium.

55. The method of claim 53, wherein electroelution is accomplished by pH mobilization of resolved proteins.

* * * * *

UNITED STATES PATENT AND TRADEMARK OFFICE
CERTIFICATE OF CORRECTION

PATENT NO.    : 6,537,432 B1  
DATED         : March 25, 2003  
INVENTOR(S)   : Luke Schneider et al.

Page 1 of 2

It is certified that error appears in the above-identified patent and that said Letters Patent is hereby corrected as shown below:

Title page,
Item [56], References Cited, U.S. PATENT DOCUMENTS, the following references are to be added:

| | | | |
|---|---|---|---|
| -- | 5,320,727 | 6/14/1994 | Peter Jackson |
| | 5,784,154 | 7/21/1998 | Janusz B. Pawliszyn |
| | 5,837,116 | 11/17/1998 | Michael G. Harrington et al. |
| | 5,993,627 | 11/30/1999 | N. Leigh Anderson et al. |
| | 6,013,165 | 1/11/2000 | John E. Wiktorowicz et al. -- |

OTHER PUBLICATIONS, the following references are to be added:

--Presentation Slides (Dr. Luke V. Schneider) from Cambridge Healthtech Institute's Second Annual Genomic Partnering Emerging and Early-Stage Companies, February 27-28, 1999, pp. 1-7.

Bai, Jian; Qian, Mark G.; Liu, Yanhui; Liang, Xiaoli and Lubman, David M.; Peptide Mapping by CNBr Degradation on a Nitrocellulose Membrane with Analysis by Matrix-Assisted Laser Desorption/Ionization Mass Spectrometry, Analytical Chemistry, May 15, 1995, Vol. 67, No. 10, pp. 1705-1710.

Chen, Xiaohui; Anderson, Vernon E. and Chen, Yong Hong; Isotope Edited Product Ion Assignment by $\alpha$-N Labelling of Peptides with [2H3(50%)2,4-Dinitrofluorobenzene, J. Am. Soc. Mass Spectrum, (1999), Vol. 10, pp. 448-542.

Eckerskorn, C.; Strupat, K.; Schleuder, D.; Hochstrasser, D.; Sanchez, J.C.; Lottspeich, F. and Hillenkamp, F.; Analysis of Proteins by Direct-Scanning Infrared-MALDI Mass Spectrometry after 2D-PAGE Separation and Electroblotting, Anal. Chem., (1997), Vol. 69, pp. 2888-2892.

Goodlett, D.R.; Bruce, J.E.; Anderson, G.A.; Rist, G.; Pasa-Tolic, L.; Fiehn, O.; Smith R.D. and Aebersold, R.; The Use of Mass Spectrometry in Proteomics; International Business Communications, Pre-conference Symposium Slides, Wednesday, December 1, 1999, pp. 1-11.

Gygi, Steven P., Functional Proteomics – Advances in the Development of Drug Leads and Diagnostic Applications Using Integrated Protein-Based Technologies - Slides, International Business Communications, 4th International Conference Slides, December 1-3, 1999, pp. 1-11.

Gygi, S.P.; Rist, B.; Gerber, S.A.; Turecek, F.; Gelb, M.H. and Aebersold, R.; Quantitative Analysis of Complex Protein Mixtures Using Isotope-coded Affinity Tags, Nature Biotechnology, October 1999, Vol. 17, pp. 994-999.

Henzel, W.J.; Billeci, T.M.; Stults, J.T.; Wong, S.C.; Grimley, C. and Watanabe, C.; Identifying Proteins from Two-dimensional Gels by Molecular Mass Searching of Peptide Fragments in Protein Sequence Databases, Proc. Natl. Acad. Sci. USA, June 1993, Vol. 90, pp. 5011-5015.

Huang, Z-H.; Shen, T.; Wu, J.; Gage, D.A. and Watson, J.T.; Protein Sequencing by Matrix-Assisted Laser Desorption Ionization-Postsource Decay-Mass Spectrometry Analysis of the N-Tris(2,4,6-trimethoxyphenyl)phosphine-Acetylated Tryptic Digests, Analytical Biochemistry (1999), Vol. 268, pp. 305-317.

Jensen, P.K.; Pasa-Tolic, L.; Anderson, G.A.; Horner, J.A.; Lipton, M.S.; Bruce, J.E. and Smith, R.D.; Probing Proteomes Using Capillary Isoelectric Focusing-Electrospray Ionization Fourier Transform Ion Cyclotron Resonance Mass Spectrometry, Anal. Chem., June 1, 1999, Vol. 71, No. 11, pp. 2076-2084.

Kilar, Ferenc, Isoelectric Focusing in Capillaries (Chapter 4), CRC Handbook of Capillary Electrophoresis: A Practical Approach, (1994), pp. 95-109.

McCormick, Randy M., Capillary Zone Electrophoresis of Peptides (Chapter 12), CRC Handbook of Capillary Electrophoresis: A Practical Approach, (1994), pp. 287-323.

UNITED STATES PATENT AND TRADEMARK OFFICE
CERTIFICATE OF CORRECTION

PATENT NO. : 6,537,432 B1
DATED : March 25, 2003
INVENTOR(S) : Luke Schneider et al.

It is certified that error appears in the above-identified patent and that said Letters Patent is hereby corrected as shown below:

Title page (cont'd),

Murphy, Constance M. and Fenselau, Catherine; Recognition of the Carboxy-Terminal Peptide in Cyanogen Bromide Digests of Proteins, Anal. Chem., (1995), Vol. 67, pp. 1644-1645.

Palmieri, Richard and Nolan, Judith A.; Protein Capillary Electrophoresis: Theoretical and Experimental Considerations for Methods Development (Chapter 13), Handbook of Capillary Electrophoresis, (1994), pp. 325-368.

Patterson, Scott D. and Aebersold, Ruedi; Mass Spectrometric Approaches for the Identification of Gel-separated Proteins, Electrophoresis, (1995), Vol. 16, pp. 1791-1814.

Shevchenko, A.; Jensen, O.N.; Podtelejnikov, A.V.; Sagliocco, F.; Wilm, M.; Vorm, O.; Mortensen, P.; Shevchenko, A.; Boucherie, H. and Mann, M.; Linking Genome and Proteome by Mass Spectrometry: Large-Scale Identification of Yeast Proteins from Two Dimensional Gels, Proc. Natl. Acad. Sci. USA, December 1996, Vol. 93, pp. 14440-14445.

Smith, R.D.; Goodlett, D.R. and Wahl, J.H.; Capillary Electrophoresis-Mass Spectrometry (Chapter 8), CRC Handbook of Capillary Electrophoresis: A Practical Approach, (1994), pp. 185-206.

Stults, J.T.; Lai, J.; McCune, S. and Wetzel, R.; Simplification of High-Energy Collision Spectra of Peptides by Amino-Terminal Derivatization, Anal. Chem., (1993), Vol. 65, pp. 1703-1708.

Wagner, D.S.; Salari, A., Gage, D.A.; Leykam, J.; Fetter, J.; Hollingsworth, R. and Watson, J.T.; Derivatization of Peptides to Enhance Ionization Efficiency and Control Fragmentation During Analysis by Fast Atom Bombardment Tandem Mass Spectrometry, Biological Mass Spectrometry, (1991), Vol. 20, pp. 419-425.

Wanders, B.J. and Everaerts, F.M.; Isotachophoresis in Capillary Electrophoresis (Chapter 5), CRC Handbook of Capillary Electrophoresis: A Practical Approach, (1994), pp. 111-127.

Zaia, Joseph, Charged Derivatives for Peptide Sequencing Using a Magnetic Sector Instrument, Methods in Molecular Biology, Vol. 61, pp. 28-40.--

Signed and Sealed this

Thirtieth Day of March, 2004

JON W. DUDAS
*Acting Director of the United States Patent and Trademark Office*